US009708644B2

(12) United States Patent
Liu et al.

(10) Patent No.: US 9,708,644 B2
(45) Date of Patent: *Jul. 18, 2017

(54) SIMULTANEOUS ACQUISITION OF BIOMETRIC DATA AND NUCLEIC ACID

(71) Applicant: LIFE TECHNOLOGIES CORPORATION, Carlsbad, CA (US)

(72) Inventors: Jason Yingjie Liu, Foster City, CA (US); Michael Harrold, San Mateo, CA (US); Chang Zhong, Stanford, CA (US); Chandani Patel, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 528 days.

This patent is subject to a terminal disclaimer.

(21) Appl. No.: 13/774,903

(22) Filed: Feb. 22, 2013

(65) Prior Publication Data
US 2013/0295572 A1 Nov. 7, 2013

Related U.S. Application Data

(60) Provisional application No. 61/601,901, filed on Feb. 22, 2012, provisional application No. 61/724,782, filed on Nov. 9, 2012.

(51) Int. Cl.
C12M 1/00 (2006.01)
C12Q 1/68 (2006.01)
C12P 19/34 (2006.01)
C07H 21/04 (2006.01)
G01N 31/22 (2006.01)
G06K 9/00 (2006.01)
G03B 29/00 (2006.01)
G01N 1/30 (2006.01)
A61B 10/00 (2006.01)
A61B 10/02 (2006.01)

(52) U.S. Cl.
CPC ........ C12Q 1/6806 (2013.01); A61B 10/0045 (2013.01); A61B 10/02 (2013.01); G01N 1/30 (2013.01)

(58) Field of Classification Search
CPC ...... A61B 10/0045; A61B 10/02; G01N 1/30; G01N 31/22; C12Q 1/6806; C12Q 1/68; C12M 1/00; C12P 19/34; G06K 9/00; G03B 29/00
USPC ..... 435/283.1, 6.1, 6.11, 91.2, 287.2, 287.3; 536/23.1, 24.3; 422/430; 382/115, 116, 382/124; 396/15
See application file for complete search history.

(56) References Cited

U.S. PATENT DOCUMENTS 7,308,123 B2 * 12/2007 Fenrich et al. ............... 382/125
8,307,854 B1 * 11/2012 Vu ........................ F16K 27/003
                                                                137/884
9,058,646 B2 * 6/2015 Harrold et al.
2002/0183624 A1 12/2002 Rowe et al.
2004/0143196 A1 7/2004 Chen
2006/0074280 A1 4/2006 Martis et al.
2006/0131391 A1 6/2006 Penuela
2007/0076923 A1 4/2007 Chiu et al.
2007/0249961 A1 10/2007 Davin et al.
2008/0194041 A1 8/2008 Guirguis
2009/0227897 A1 9/2009 Wendt et al.
2009/0257626 A1 10/2009 Sherlock et al.
2010/0030111 A1 2/2010 Perriere et al.
2010/0041131 A1 2/2010 Brown
2010/0098831 A1 4/2010 Anderson et al.
2010/0184126 A1 7/2010 Rutty et al.
2010/0191147 A1 7/2010 Miyoshi et al.
2011/0163163 A1 7/2011 Rowe
2011/0172510 A1 7/2011 Chickering et al.
2012/0103421 A1 * 5/2012 Grenz ................... B01L 3/0275
                                                                137/1
2012/0165697 A1 6/2012 Kelly et al.
2013/0078625 A1 * 3/2013 Holmes et al. ............. 435/6.11
2013/0101184 A1 4/2013 Harrold et al.
2013/0106568 A1 5/2013 Harrold et al.
2013/0202182 A1 8/2013 Rowe et al.
2016/0154990 A1 6/2016 Harrold et al.

FOREIGN PATENT DOCUMENTS

| DE | 202005020535 U1 | 5/2006 |
| EP | 1504722 A2 | 2/2005 |
| WO | 9907282 A1 | 2/1999 |
| WO | 2006061771 A2 | 6/2006 |
| WO | 2007120865 A2 | 10/2007 |
| WO | 2009018473 A1 | 2/2009 |
| WO | 2009021130 A1 | 2/2009 |
| WO | 2011026169 A1 | 3/2011 |
| WO | WO 2011026169 * | 3/2011 |

OTHER PUBLICATIONS

Wang, Y. et al., "Data Acquisition and Quality Analysis of 3-Demensional Fingerprints", Florida: IEEE conference on Biometrics, Identity and Security. http://vis.uky.edu/~realtime3d/Doc/3D_Fingerprint_Quality.pdf, Retrieved Mar. 2000, 10 pages.
Wang, Y. et al., "Fit-sphere unwrapping and performance analysis of 3D fingerprints", Optical Society of America, vol. 49, Feb. 1, 2010, pp. 592-600.

* cited by examiner

Primary Examiner — Narayan Bhat
(74) Attorney, Agent, or Firm — Priya Subramony; Peter G. Foiles

(57) ABSTRACT

Systems, methods, and kits are disclosed for collection, labeling and analyzing biological samples containing nucleic acid in conjunction with collecting at least one ridge and valley signature of an individual. Such devices and methods are used in forensic, human identification, access control and screening technologies to rapidly process an individual's identity or determine the identity of an individual.

23 Claims, 20 Drawing Sheets

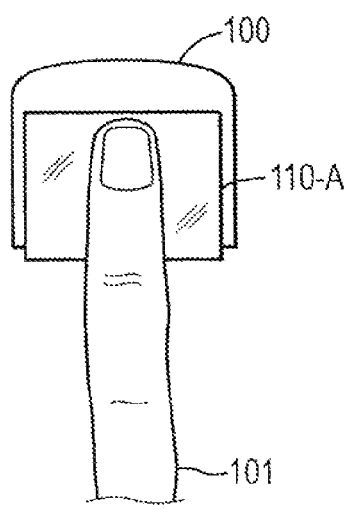
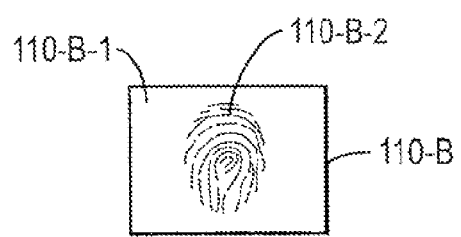
FIG. 1A
FIG. 1B

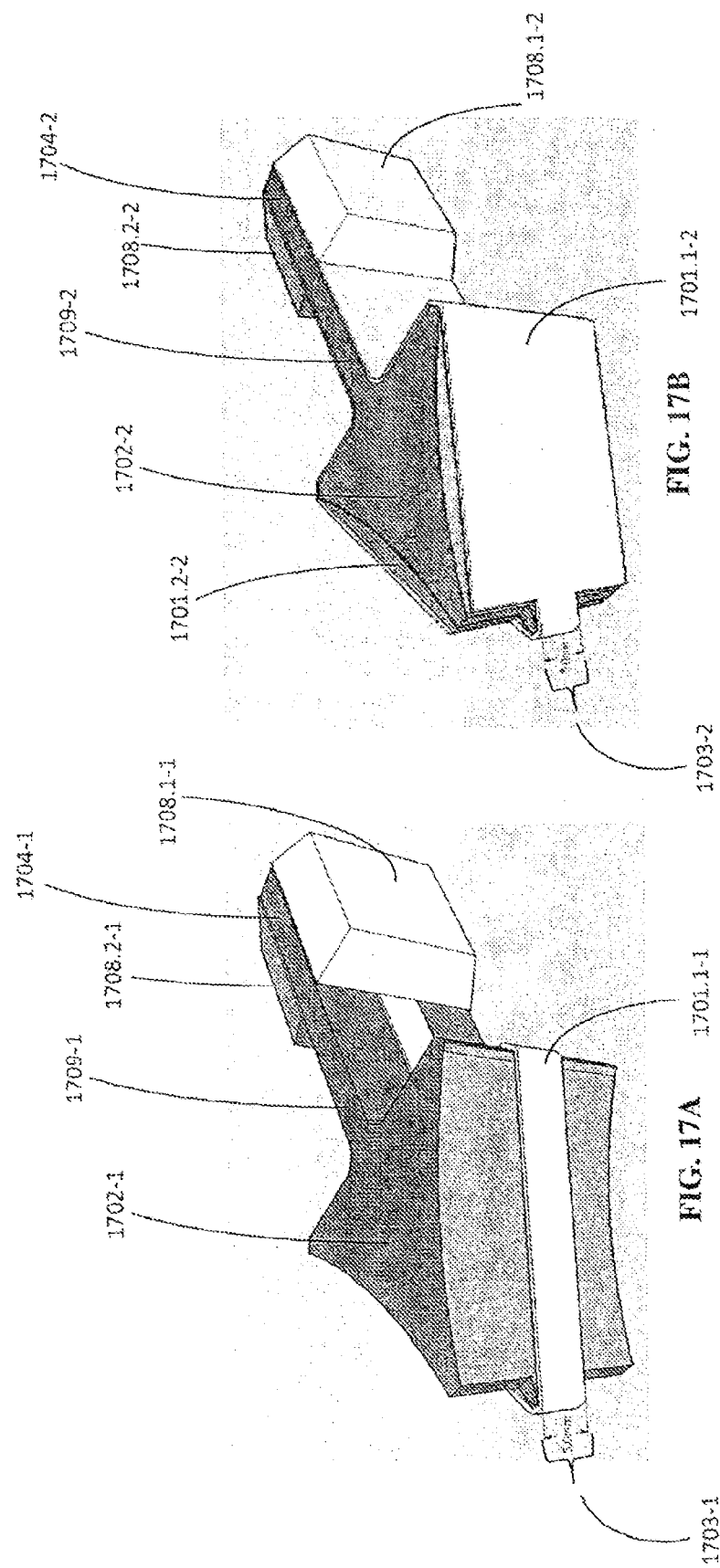

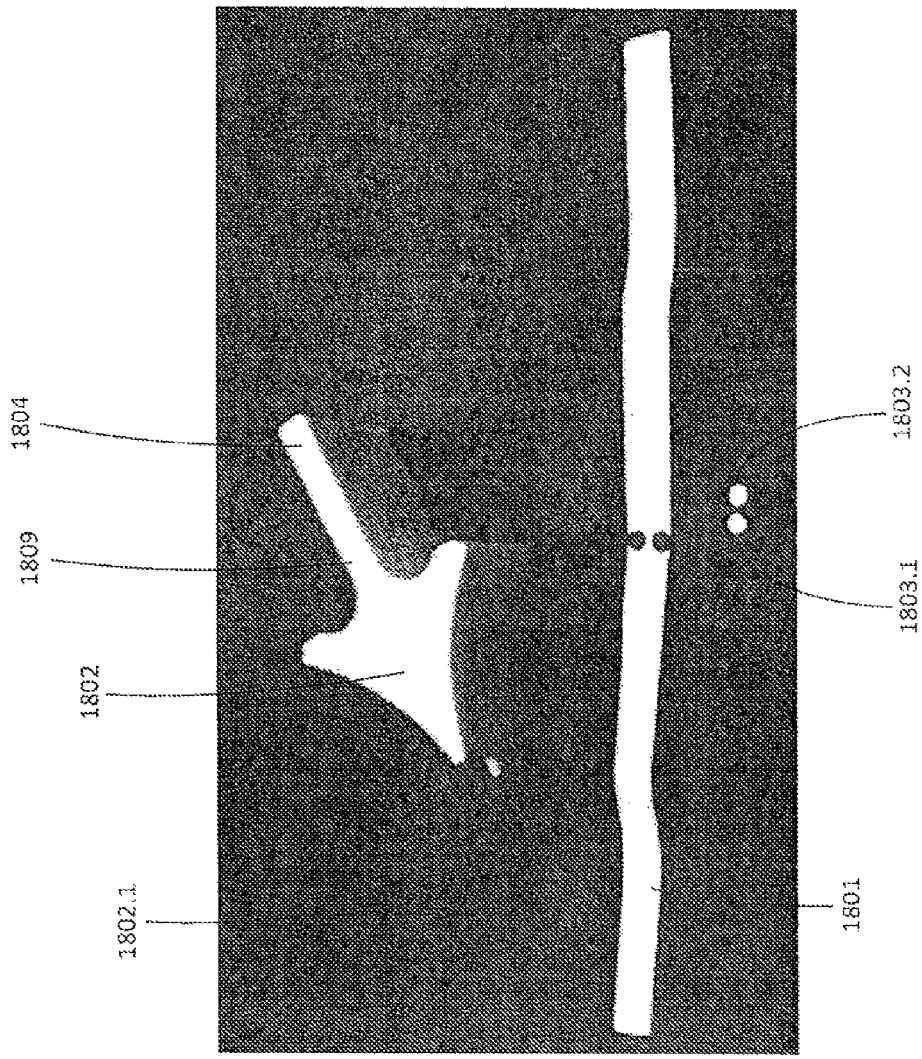

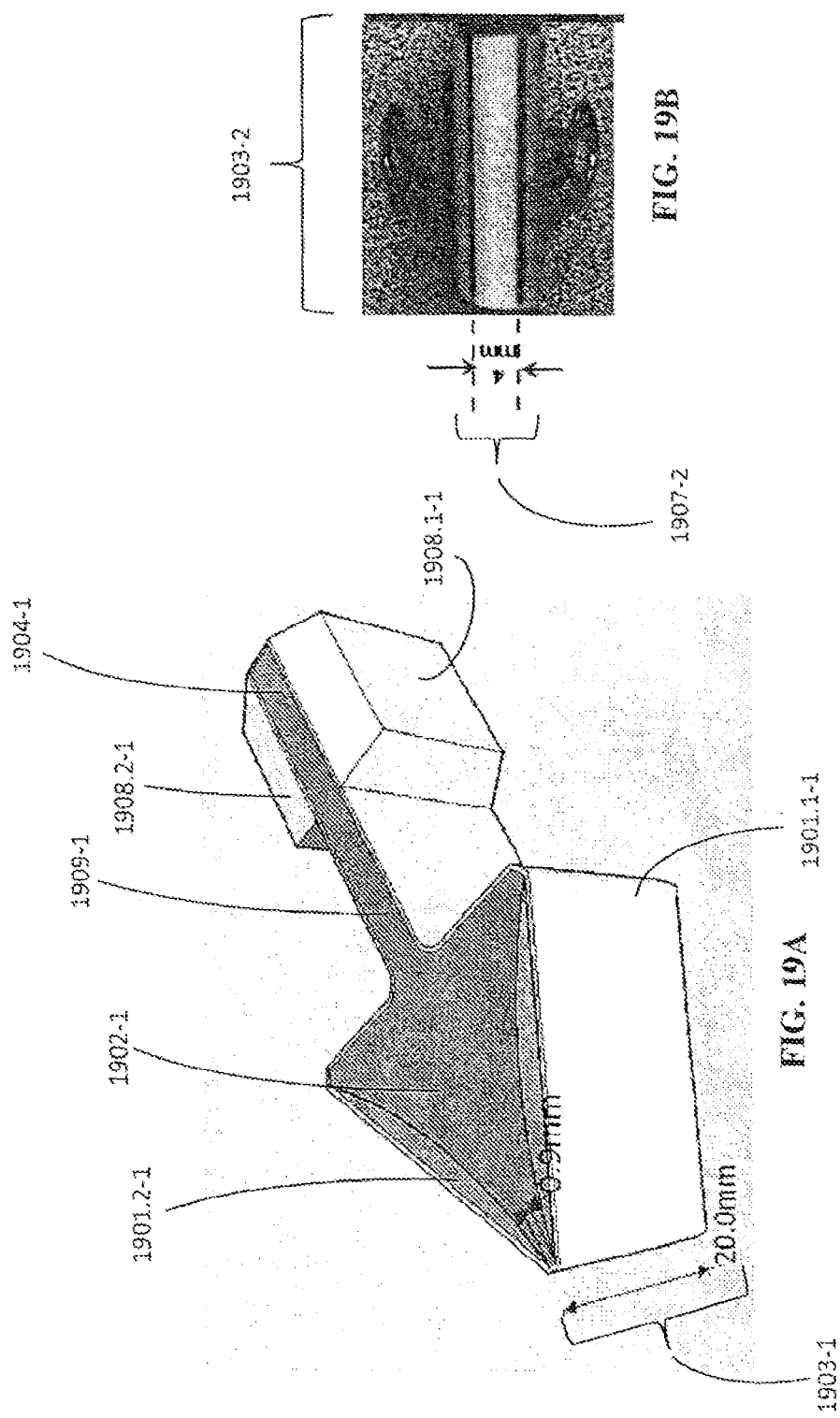

SIMULTANEOUS ACQUISITION OF BIOMETRIC DATA AND NUCLEIC ACID

This application claims the benefit of priority under 35 U.S.C. §119(e) to U.S. Provisional Application No. 61/601,901 entitled "Simultaneous Acquisition of Biometric Data and Nucleic Acid", filed on Feb. 22, 2012, and to U.S. Provisional Application No. 61/724,782 entitled "Simultaneous Acquisition of Biometric Data and Nucleic Acid", filed on Nov. 9, 2012, each disclosure of which is incorporated by reference in its entirety.

Cross Reference. This application is also related to a United States utility application filed on even date, inventor, Jason Yingjie Liu, which is entitled "Sample Collection Devices, Kits and Methods of Use", Life Technologies Ser. No. 13/774,823, which disclosure is incorporated by reference in its entirety.

The section headings used herein are for organizational purposes only and should not be construed as limiting the subject matter described herein in any way.

FIELD

The present teachings relate to devices and methods for obtaining biometric data and nucleic acids for use in human identification and forensic science.

INTRODUCTION

Forensic evidence and biometric data are often used together to identify perpetrators of criminal activities as well as for the identification of missing persons, victims of mass disasters, paternity testing and to exonerate the innocent. The ability to simultaneously collect biometric data such as fingerprints, an iris or retinal scan, an image or photo of an individual can, with a biological sample(s) such as forensic evidence including but not limited to blood, tissue, hair, body fluid or a buccal sample, provide a system for expediting identification, access control, and screening of individuals. Furthermore, maintaining identification of related data points and correlating the data with the respective biological samples can be complicated and susceptible to errors which compromise the chain of custody. Therefore, there remains a need to accurately collect, associate correctly, and process biometric data and biological samples from a single individual in one collection step or workflow.

SUMMARY

In one aspect, the invention provides a sample concentration device for concentrating a biological sample containing nucleic acid of an individual including an active collection component including a first surface area configured to be an active collection surface area; a handling component; where the active collection component is detachably connected to at least one of a first or second portion of the handling component; and where the device is configured to: a) collect the biological sample from at least a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area. In some embodiments, the substrate has at least a first surface area configured to: a) permit penetration of an energy wave configured to image at least one ridge and valley signature of an appendage of the individual through the substrate to image the appendage in contact with the substrate; and b) collect the biological sample from the appendage. The active collection component may include material configured to be compatible with the amplification reaction conditions.

In various embodiments, the active collection component may be configured in a sheet form. In some embodiments, the active collection component may include fibrous material. The fibrous material of the active collection component may include natural fibers, synthetic polymeric fibers or a combination thereof. In some embodiments, the fibrous material may be Nylon® fibers, cotton, Dacron, or paper, and optionally, where the fibrous material is chemically treated. In some embodiments, the fibrous material may be selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof.

In some embodiments, the biological sample may not be transferred from the at least first portion of the active collection surface area before being subjected to the amplification reaction. In other embodiments, the biological sample may be transferred from the at least first portion of the active collection surface to another receptacle or material before analysis of the sample. In some embodiments, the device may be configured to detach the active collection component from the first portion of the handling component to permit amplification of the nucleic acids of the biological sample. In other embodiments, the device may be configured to detach the active collection component from both the first and the second portion of the handling component, which separates the active collection component entirely from the handling component. In yet other embodiments, the device may be configured to detach the active collection component from the second portion of the handling component.

In some embodiments, the active collection surface area may be configured to be the surface area encompassing an exterior edge of an angled fold of the active collection component, where the angled fold is formed over a first portion of the handling component. In some embodiments, a length of the active collection component along the angled fold may be about 20 mm or less. In other embodiments, a length of the active collection component along the angled fold may be about 5 mm or less. In some embodiments, the exterior edge of the angled fold may form an acute angle. In other embodiments, the exterior edge of the angled fold may include a roiled edge having a diameter of less than about 3 mm. In various embodiments, the active collection surface area may be at least about 90% smaller than the at least first surface area of the substrate. In other embodiments, the active collection surface area may be at least about 200% smaller than the at least first surface area of the substrate.

In some embodiments of the sample concentration device, the active collection component may be attached to the handling component via a pre-scored junction segment, where the pre-scored junction segment may be fractured to detach the active collection component from the second portion of the handling component. In some embodiments, the active collection component may be attached to the handling component via friction, vacuum or static charge. In other embodiments, the active collection component may be attached to the handling component with an adhesive. In yet other embodiments, the active collection component may be attached to the handling component via securing elements on the handling component. In some embodiments, the securing elements may be selected from: O-rings, clips, snaps, pressurized fittings, or removable adhesive. In some embodiments, the active collection component has a disk shaped collection area.

In various embodiments of the sample concentration device, the at least first portion of the active collection surface area may be one or more punches taken from the surface area encompassing the angled fold. The at least first portion of the active collection surface area may be configured to fit within a reaction volume of about 2 ul to about 100 ul. In other embodiments, the at least first portion of the active collection surface area may be configured to fit within a reaction volume of about 2 ul to about 50 ul. In other embodiments, the active collection surface area may also be configured to provide at least a second portion of the active collection surface area for archiving.

In various embodiments of the sample concentration device, the active collection component may be connected to the first portion of the handling component by a detachable connector component. In some embodiments, the active collection component may be connected to the first portion of the handling component by at least a second surface area of the active collection component in other embodiments, the active collection component may be attached to the first or the second portion of the handling component via clips or other pressurized fittings on the handling component which may be removed or released after sample collection. In other embodiments, the active collection component may be connected to the first portion of the handling component by at least a second surface area of the active collection component.

In various embodiments, the first portion of the handling component includes one or more layers of absorbent material underlying the active collection component. In various embodiments, the second portion of the handling component may be detachable connected to the active collection component. In various embodiments, the first portion of the handling component includes a stiffening support for the active collection component.

In various embodiments of the sample concentration device, the active collection component may be attached to the handling component via a pre-scored junction segment, wherein the pre-scored junction segment may be fractured to detach the active collection component from the handling component.

In various embodiments of the sample concentration device, the active collection component, the handling component, or both may include an identifier to associate the sample with the substrate from which the sample was collected, where the identifier is alphanumeric, graphical, magnetic, or electromagnetic. In some embodiments, the identifier is a barcode. In various embodiments, the active collection component may include the identifier. In other embodiments, the at least first portion of the active collection component may include the identifier.

In yet another aspect, the invention provides a handling component including a support portion and a handle portion, where the handling component is configured to support an active collection component for collection of a sample. In some embodiments, the support portion of the handling component tapers to a thin edge. The support portion may taper to a thin edge having a width less than about 20 mm wide and having a thickness less than about 5 mm. In other embodiments, the support portion may taper to a thin edge having a width less than about 5 mm wide and a thickness of less than about 3 mm thick. The handle portion may be less than about 20 mm long. In some embodiments, the handling component is plastic.

In another aspect, the invention provides a kit including a sample concentration device which includes an active collection component having a first surface area configured to be an active collection surface area; a handling component; where the active collection component is detachably connected to at least one of a first or a second portion of the handling component; and where the device is configured to: a) collect the biological sample from at least a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area.

In some embodiments of the kit, the sample concentration device may be configured to detach the active collection component from the first portion of the handling component to permit analysis of the sample. In other embodiments, the device may be configured to detach the active collection component from both the first and the second portion of the handling component, which separates the active collection component entirely from the handling component. In yet other embodiments, the device may be configured to detach the active collection component from the second portion of the handling component. In various embodiments, the active collection component may include material configured to be compatible with reaction conditions of the analysis. In various embodiments, the active collection component may be configured in a sheet form. In some embodiments, the active collection component may include fibrous material. The fibrous material of the active collection component may include natural fibers, synthetic polymeric fibers or a combination thereof. In some embodiments, the fibrous material may be Nylon® fibers, cotton, Dacron, or paper, and optionally, where the fibrous material is chemically treated, in some embodiments, the fibrous material may be selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof.

In some embodiments of the kit, the active collection surface area of the sample concentration device may be configured to be the surface area encompassing an exterior edge of an angled fold of the active collection component, where the angled fold is formed over the first portion of the handling component. In some embodiments, a length of the active collection component along the angled fold may be about 20 mm or less. In other embodiments, a length of the active collection component along the angled fold may be about 5 mm or less. In some embodiments, the exterior edge of the angled fold may form an acute angle, in other embodiments, the exterior edge of the angled fold may include a rolled edge having a diameter of less than about 3 mm. In various embodiments, the active collection surface area may be at least about 50% smaller than the at least first surface area of the substrate. In other embodiments, the active collection surface area may be at least about 90% smaller than the at least first surface area of the substrate.

In some embodiments of the kit, the active collection component of the sample concentration device may be attached to the handling component via a pre-scored junction segment, where the pre-scored junction segment may be fractured to detach the active collection component from the second portion of the handling component. In some embodiments, the active collection component may be attached to the handling component via friction, vacuum or static charge. In some embodiments the active collection component may be attached to the handling component with securing elements on the handling component. In some embodiments, the securing elements may be selected from O-rings, clips, snaps, pressurized fittings, or removable adhesive. In some embodiments, the active collection component has a disk shaped collection area. In some embodiments of the kit, the at least first portion of the active collection surface area of the sample concentration device may be configured to fit within a reaction volume of about 2 ul to about 100 ul. In other embodiments, the at least first portion of the active collection surface area may be configured to fit within a reaction volume of about 2 ul to about 50 ul. In other embodiments, the active collection surface area may also be configured to provide at least a second portion of the active collection surface area for archiving.

In various embodiments of the kit, the active collection component of the sample concentration device may be connected to the first portion of the handling component by a detachable connector component. In some embodiments, the active collection component may be connected to the first portion of the handling component by at least a second surface area of the active collection component. In other embodiments, the active collection component may be attached to the first or the second portion of the handling component via securing elements on the handling component which may be removed or released after biological sample collection. In some embodiments, the securing elements may be selected from O-rings, clips, snaps, pressurized fittings, or removable adhesive. In other embodiments, the active collection component may be connected to the first portion of the handling component by at least a second surface area of the active collection component.

In various embodiments, the first portion of the handling component includes one or more layers of absorbent material underlying the active collection component. In various embodiments, the second portion of the handling component may be detachably connected to the active collection component. In various embodiments, the first portion of the handling component includes a stiffening support for the active collection component.

In some embodiments, the kit may include one or more collection assistance liquids. In some embodiments, the collection assistance liquid is water, ethanol, or acetonitrile. In other embodiments, the kit may include reagents for stabilizing the sample on the active collection component of the sample concentration device for archiving or shipping, in other embodiments, the kit further may include reagents for analysis of the sample. In other embodiments, the kit may further include at least one enclosure to protect the active collection component, the handling component, or both from contamination prior to use. In yet other embodiments, the kit may include at least one enclosure to protect the active collection component from contamination while archiving or shipping. In various embodiments of the kit, any combination of the active collection component, the handling component or the at least one enclosure may include an identifier to associate the sample with the substrate from which the sample was collected, where the identifier is alphanumeric, graphical, magnetic, or electromagnetic. In some embodiments, the identifier is a barcode.

In a further aspect, the invention provides a kit including a handling component including a support portion and a handle portion, where the handling component is configured to support an active collection component for collection of a biological sample, and optionally, instructions for use. In some embodiments, the support portion of the handling component tapers to a thin edge. The support portion may taper to a thin edge having a width less than about 20 mm wide and having a thickness less than about 5 mm. In other embodiments, the support portion may taper to a thin edge having a width less than about 5 mm wide and a thickness of less than about 3 mm thick. The handle portion may be less than about 20 mm long. In some embodiments, the handling component is plastic. In some embodiments, the kit further includes one or more active collection components. The active collection component may include an active collection surface area. In some embodiments, the active collection component is a paper material selected from Whatman® paper, including W-903 paper, FTA™ paper, FTA™ Elute paper, FTA™DMPK paper, Ahlstrom A-228 paper, M-TFN paper, FTA® paper, FP705™ paper, Bode DNA collection paper, nitrocellulose paper, nylon paper, cellulose paper, Dacron paper, cotton paper, and polyester papers, and combinations thereof. The material for the active collection component may have a strip shape and may be of uniform width along its length. Alternatively, the material may be fabricated with a uniform width throughout its length, except at the active collection surface area supported by the tapered edge of the support portion of the handling component, where it may have a decreased width relative to the remainder of the active collection component. The kit may further include securing elements to attach the active collection component to the handling component, selected from the group of O-rings, snaps, clips, guideholes and securing pins, and double sided tape.

In yet another aspect, the invention provides a Kit for collection of a biological sample including nucleic acid and at least one ridge and valley signature of an individual including: a substrate having at least a first surface area configured to: a) permit penetration of an energy wave configured to image the at least one ridge and valley signature of an appendage of the individual through the substrate to image the appendage in contact with the substrate; and b) collect the biological sample from the appendage; a sample concentration device, and optionally, reagents for archiving, stabilizing for shipping and/or amplifying the nucleic acid. The sample concentration device may include an active collection component having a first surface area configured to be an active collection surface area; a handling component; where the active collection component is detachably connected to at least one of a first or a second portion of the handling component; and where the device is configured to: a) collect the biological sample from at least a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area.

In some embodiments of the kit, the substrate may be polymeric film or glass. In other embodiments, the polymeric film substrate may be a synthetic polymeric film. In various embodiments, the substrate may be a non-adhesive polymeric film. In some embodiments, the substrate may be configured to conform to a scanning surface of an imaging component.

In various embodiments of the kit, the substrate may further include a frame configured to support the substrate. In various embodiments, the frame may be formed from a material selected from a plastic, a paper, a polyolefin, a polystyrene, a metal, a metal alloy, a glass, a silicon, or combinations thereof. In some embodiments, the substrate frame may further include a cover component configured to protect the surface of the substrate before and after collection of the ridge and valley signature and the biological sample.

In various embodiments of the kit, the at least one surface area of the substrate may be sectioned into a first contact surface area configured to substantially encompass the surface area that the appendage contacts, and a second surface area configured to substantially surround the first contact surface area.

In various embodiments of the kit, the substrate or the sample concentration device may be suitable for shipping or archiving the biological sample. In other embodiments, the substrate, the sample concentration device, or both may include an identifier to associate the biological sample of the individual with the at least one ridge and valley signature of the individual, wherein the identifier is alphanumeric, graphical, magnetic, or electromagnetic. In some embodiments, the identifier is a barcode.

In another aspect, the invention provides a system for collection of a biological sample including nucleic acid and at least one ridge and valley signature of an individual including: at least a first imaging component comprising a scanning surface configured to permit an energy wave to penetrate the scanning surface, where the energy wave is configured to image the at least one ridge and valley signature of an appendage of the individual; a substrate having at least a first surface area, wherein the substrate is configured to: a) permit the energy wave to penetrate the substrate to image the appendage in contact with the substrate; and b) collect the biological sample from the appendage, where the system is configured to collect at least one ridge and valley signature by imaging the appendage through the scanning surface and the substrate while the appendage is positioned upon the substrate. The system may further include a sample concentration device. The sample concentration device may include an active collection component having a first surface area configured to be an active collection surface area; a handling component; where the active collection component is detachably connected to at least one of a first or a second portion of the handling component; and where the device is configured to: a) collect the biological sample from at least a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area.

In some embodiments of the system, the scanning surface may be formed from a material selected from a plastic, a polyolefin, a polystyrene, a metal, a metal alloy, a glass, a silicon material or combinations thereof. In other embodiments, the material of the scanning surface may be transparent or translucent.

In some embodiments of the system, the at least one surface area of the substrate may be sectioned into a first contact surface area configured to substantially encompass the surface area contacted by the appendage, and a second surface area configured to substantially surround the first contact surface area. In some embodiments, the substrate may be polymeric film or glass. In various embodiments, the polymeric film substrate may be a synthetic polymeric film. In other embodiments, the polymeric film substrate may be non-adhesive.

In various embodiments of the system, the substrate may be configured to conform to a scanning surface of an imaging component. In some embodiments, the substrate may further include a frame configured to support the substrate.

In various embodiments of the system, the frame is formed from a material selected from a plastic, a paper, a polyolefin, a polystyrene, a metal, a metal alloy, a glass, a silicon or combinations thereof. In some embodiments, the substrate frame may further include a cover component configured to protect the surface of the substrate before and after collection of the ridge and valley signature and the biological sample.

In various embodiments of the system, the substrate and/or the sample concentration device may be suitable for shipping and/or for archiving the biological sample.

In various embodiments of the system, the substrate, the sample concentration device, or both may include an identifier to associate the biological sample of the individual with the at least one ridge and valley signature of the individual, where the identifier is alphanumeric, graphical, magnetic, or electromagnetic. In some embodiments, the identifier is a barcode.

In various embodiments of the system, the system further includes a processor configured to transmit the ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control and any combination thereof.

In another aspect, the invention provides a method of collecting a biological sample comprising nucleic acid and at least one ridge and valley signature of an individual. In some embodiments, the methods include identifying the individual. In various embodiments, the method for collection of a biological sample comprising at least one nucleic acid and at least one ridge and valley signature of an individual includes providing at least a first imaging component. The at least first imaging component is configured to provide an energy wave and comprises a scanning surface configured to permit the energy wave to penetrate the scanning surface. The method includes providing a substrate configured to collect the biological sample from an appendage of the individual and configured to permit the energy wave to penetrate the scanning surface, where the substrate is positioned over the scanning surface. The method includes the steps of positioning the appendage of the individual upon the substrate, thereby depositing the biological sample upon the substrate; collecting the at least one ridge and valley signature from the appendage imaged by the energy wave; and concentrating the biological sample from the substrate to a sample concentration device. The sample concentration device may include an active collection component having a first surface area configured to be an active collection surface area; a handling component; where the active collection component is detachably connected to at least one of a first or a second portion of the handling component; and where the device is configured to: a) collect the biological sample from at least a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area.

In some embodiments, the method may also include the step of prewetting the substrate or the sample concentration device with ethanol, water, or acetonitrile when concentrating the biological sample from the substrate to the sample concentration device. In some embodiments, ethanol is used to prewet the substrate or the sample concentration device. In other embodiments, wafer is used to prewet the substrate or the sample concentration device.

In other embodiments, the method may also include the step of the detaching the active collection component from at least one of a first or a second portion of the handling component of the sample concentration device.

In some embodiments the method may also include the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

The method may further Include the step of providing an identifier to associate the biological sample of the individual with the at least one ridge and valley signature of the individual, wherein the identifier is alphanumeric, graphical, magnetic, or electromagnetic. The identifier may be a barcode.

The method may further include shipping the substrate containing the biological sample to another location for archiving or testing prior to the step of concentrating the biological sample.

The method may further include the step of archiving the substrate containing the biological sample prior to the step of concentrating the biological sample.

The method may further include the step of subjecting the biological sample to at least one of a polymerase chain reaction, a DNA sequencing reaction, STR analysis, SNP analysis, or Indel analysis after the sample has been concentrated to the sample concentration device.

In some embodiments, method may further include the step of transmitting the at least one ridge and valley signature of the individual to at least one database comprising ridge and valley signatures selected from the group consisting of a forensic, criminal, identity, child identity, missing persons, Immigration, department of motor vehicles, terrorist, paternity, arrestee, convict database, access control or any combination thereof.

In some embodiments, the optical scanner comprises a LED, laser diode, incandescent light source, or a multispectral imager. The at least first imaging component may alternatively be a camera, an active pixel imager, a CMOS imager, an imager that images in multiple wavelengths, a CCD camera, a photo detector array, and a TFT imager. The at least one ridge and valley signature may be collected electronically. The scanning surface of the at least first imaging component may be formed from a material selected from a plastic, a polyolefin, a polystyrene, a metal, a metal alloy, a glass, a silicon or combinations thereof. In some embodiments, the material of the scanning surface is transparent or translucent.

In various embodiments, the substrate may be polymeric film or glass. In some embodiments, the polymeric film substrate may be a synthetic polymeric film. In other embodiments, the polymeric film substrate may be a natural polymer, including but not limited to a starch, an agarose, an alginate, a carrageenan, and the like. In some embodiments, the polymeric film substrate may be non-adhesive. In various embodiments, the substrate may be transparent or translucent.

In another aspect, the invention provides a method of identifying an individual, comprising the steps of: providing at least a first imaging component configured to provide an energy wave and includes a scanning surface configured to permit the energy wave to penetrate the scanning surface; providing a substrate configured to collect the biological sample from an appendage of the individual and configured to permit the energy wave to penetrate the scanning surface, where the substrate is positioned over the scanning surface; positioning the appendage of the individual upon the substrate, thereby depositing the biological sample upon the substrate; collecting the at least one ridge and valley signature from the appendage imaged by the energy wave; and concentrating the biological sample from the substrate to a sample concentration device; and subjecting the concentrated biological sample to an analysis thereby providing identification of the individual. The sample concentration device may include an active collection component having a first surface area configured to be an active collection surface area; a handling component; where the active collection component is detachably connected to at least one of a first or a second portion of the handling component; and where the device is configured to: a) collect the biological sample from at least a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area.

In some embodiments, the analysis is at least one of a polymerase chain reaction, a DNA sequencing reaction, STR analysis, SNP analysis, or Indel analysis.

In some embodiments, method may further include the step of transmitting the at least one ridge and valley signature of the individual to at least one database comprising ridge and valley signatures selected from the group consisting of a forensic, criminal, identity, child identify, missing persons, immigration, department of motor vehicles, terrorist, paternity, arrestee, convict database, access control or any combination thereof.

In yet another aspect, the invention provides a method of collecting a biological sample including the steps of: providing a sample concentration device which includes an active collection component having a first surface area configured to be an active collection surface area; a handling component; where the active collection component is detachably connected to at least one of a first or a second portion of the handling component; and where the device is configured to: a) collect the biological sample from at least a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area; providing a substrate including a sample; and collecting the sample by contacting an active collection surface area of an active collection component of the sample concentration device to at least a first surface area of the substrate.

In some embodiments of the method for collection of a sample, the method may further include the step of detaching the active collection component from at least one of a first or a second portion of the handling component of the sample concentration device. The method may further include the step of separating at least a first portion of the active collection surface area from the active collection component.

The method for collection of a sample may further include the step of providing an identifier to associate the sample collected to the active collection surface area with the substrate from which the sample was collected, where the identifier is alphanumeric, graphical, magnetic, or electromagnetic. The identifier may be a barcode.

In various embodiments of the method for collection of a sample, the method may further include the step of shipping the sample concentration device including the sample to another location for archiving or testing. In other embodiments, the method may further include the step of shipping the active collection component including the sample to another location for archiving or testing.

In yet another aspect, the invention provides a process for manufacturing a sample concentration device, including the steps of fabricating a handling component including a support portion and a handle portion; fabricating an active collection component including an active collection surface area in a strip; placing the active collection surface area of the active collection component over the support portion to create an angled edge; and securing the active collection component to at least one of the support portion or the handle portion of the handling component. In some embodiments, the handling component is plastic. In some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the active collection component may be fabricated to have a uniform width. In other embodiments, the active collection component may be fabricated where the active collection surface area has a smaller width than the rest of the active collection component.

In another aspect, the invention provides a process for manufacturing a handling component of a sample concentration device including the steps of fabricating a support portion and a handle portion. In some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the handling component is plastic.

In the following description, certain aspects and embodiments will become evident, it should be understood that a given embodiment need not have all aspects and features described herein. It should be understood that these aspects and embodiments are merely exemplary and explanatory and are not restrictive of the invention.

There still exists a need for improved systems, kits, and methods for collecting fingerprint and biological sample data for purposes of identifying and confirming the identify of a human individual.

BRIEF DESCRIPTION OF THE DRAWINGS

The skilled artisan will understand that the drawings described below are for illustration purposes only. The drawings are not intended to limit the scope of the present teachings in any way.

FIG. 1 shows (A) a graphical representation of a simultaneous acquisition of a fingerprint and a biological sample containing nucleic acid and (B) illustrates a substrate after the fingerprint and biological sample has been deposited.

FIG. 17 shows a graphical representation of two embodiments (A) and (B) of edge swabs, which are sample concentration devices.

FIG. 18 is a graphical representation of an embodiment of the edge swab after use, and demonstrating retrieval of portions of the active collection surface area for analysis.

FIG. 19 is a graphical representation of an embodiment (A) and (B) of an edge swab and a graphical representation of a rolled edge swab.

DETAILED DESCRIPTION

Figures 2A, 2B:
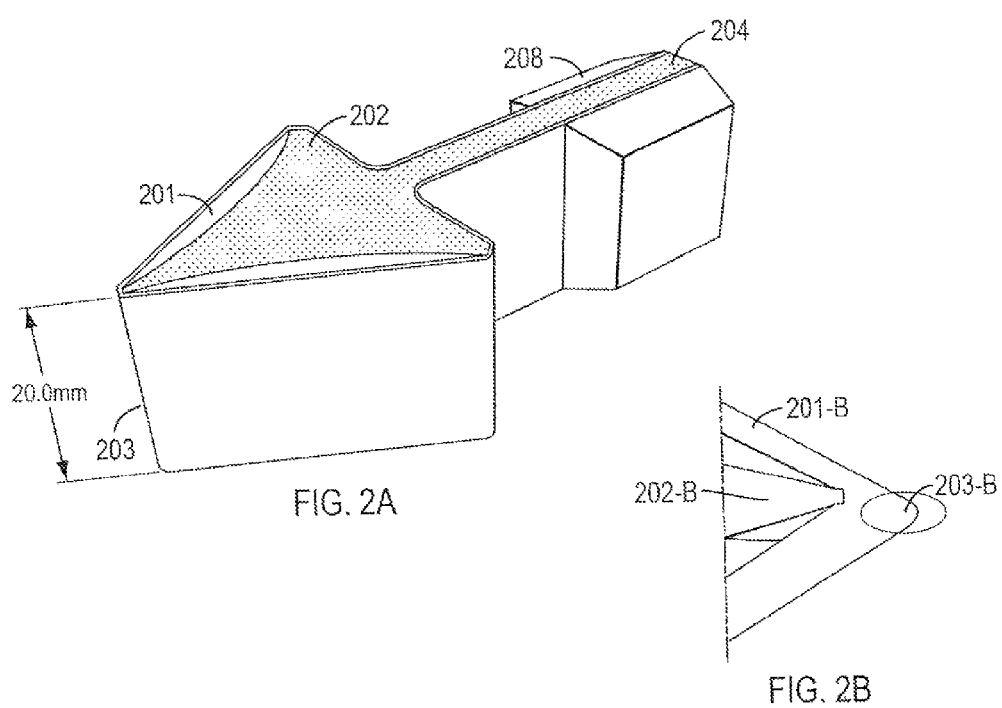
FIG. 2 shows (A) a graphical representation of an edge swab, which is one example of a sample concentration device and (B) is a graphical representation of an enlargement of the active surface area of the active collection component of the swab.

For the purposes of interpreting this specification, the following definitions will apply and whenever appropriate, terms used in the singular will also include the plural and vice versa, in the event that any definition set forth below conflicts with the usage of that word in any other document including any document incorporated herein by reference, the definition set forth below shall always control for purposes of interpreting this specification and its associated claims unless a contrary meaning is clearly intended (for example in the document where the term is originally used), it is noted that as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that in some specific instances, the embodiment or embodiments can be alternatively described using the language "consisting essentially of" and/or "consisting of."

As used herein, "DNA" and "nucleic acid" are used interchangeably.

As used herein "oligonucleotide" and "polynucleotide" are interchangeable and generally refers to a polymer of nucleotide subunits having a fragment size of about or less than 200 base pairs.

As used herein, "biological sample" refers to a component originating from either within or on the body of an individual.

As used herein, "body fluid" refers to liquids originating within the body of an individual.

As used herein, "digital imaging apparatus" refers to an apparatus capable of digitizing an image of an object.

As used herein, "DNA sequencing" refers to the determination of the sequential identify of nucleotides in a molecule of DNA.

As used herein, "filter paper" refers to a semi-permeable paper.

As used herein, "a housing" refers to a structure surrounding at least in part an apparatus capable of performing a physical movement or carrying out a physical action including but not limited to illuminating, scanning and the like.

As used herein, "identifier" refers to a label capable of use in cataloging/correlating like-labeled data or data from a single source.

As used herein, "image capturing device" refers to a type of camera or scanning device.

As used herein, "imaging component" refers to art apparatus capable of performing at least one of capturing, developing, storing, retrieving and transmitting an image.

As used herein, "Indel" refers to an insertion or deletion of a segment of nucleic acid, usually DNA, within a nucleic acid sequence.

As used herein, "isolated" refers to separation of nucleic acid from either or both naturally occurring materials or environmental chemicals/substances.

As used herein, "light emitting diodes" refers to LEDs, a semiconductor light source.

As used herein, "multispectral illuminator" refers to a plurality of frequencies/wavelengths across the electromagnetic spectrum used to capture image data.

As used herein, "optically collecting" refers to obtaining data, such as a ridge and valley signature or an image through illuminating the data or image and capturing the result.

As used herein, "appendage" refers to one of several most distal parts of a limb, and includes a finger or toe.

As used herein, "photographic apparatus" refers to an LED camera, a digital camera, a still camera, a video camera and a virtual camera.

As used herein, "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

As used herein, "ridge and valley signature" refers to the friction ridges also known as surface contours on the palmar surface of the fingers, surface of the palm and hand and plantar surface of the feet and toes. In particular, the friction ridges provided by the impressions made from imaging one or more fingers are known as fingerprints.

As used herein, "SNP analysis" refers to the evaluation of the presence or absence of a single nucleotide polymorphism (SNP) marker following amplification of the locus containing the SNP marker As used herein, "SNP analysis" refers to the evaluation of the alleles of a short tandem repeat (STR) marker following amplification of the locus containing the STR marker.

As used herein, "succession" refers to a sequence of steps performed.

As used herein, "substrate suitable for electrophoresis" refers to a matrix which can support the migration of species, including but not limited to nucleic acids when exposed to an electrical current such as electrophoresis.

As used herein, "topological impression" refers to the ridge and valley topography of a finger, palm, toe or foot.

Reference will now be made to various embodiments, examples of which are illustrated in the accompanying drawings.

The present teachings relate to systems, kits, and methods for collecting a biological sample containing nucleic acid and at least one ridge and valley signature from an individual. A system according to the invention can find use in, but is not limited to, forensic, criminal, identify, child identity, missing persons, immigration, department of motor vehicles, terrorist, paternity, arrestee, access control or convict database applications. Furthermore, the ability to rapidly correlate the ridge and valley signature of an individual, such as a finger or toe print, palm or sole print with a nucleic acid profile, such as a DNA fingerprint, can provide rapid screening and identification of persons of nefarious intent, suspected of having conducted illegal activities, suspects in criminal investigations and persons of interest and can prevent access of such persons to situations where they might harm others, such as an airline flight, entrance into a high security access area or other sites where access is restricted or poses a security risk. Rapid correlation can also aid in identification and resolution of missing person investigations, in other applications, rapid correlation of nucleic acid profiles and a valley and ridge signature can be used in assisting proper familial identification in immigration and political asylum investigations.

Improvements are needed for collection of biological samples containing nucleic acid while also obtaining biometric information such as a fingerprint. In particular, it is advantageous to obtain the biological sample non-invasively. It has been found that, under suitable conditions, when a ridge and valley signature of an appendage of an individual is imaged through a substrate and scanning surface, that sufficient nucleic acid is deposited, when the appendage contacts the substrate, to provide a DNA profile having sufficient signal to identify the individual. In some embodiments, devices, systems, and methods are disclosed to concentrate the biological sample, once deposited upon a substrate, to a very small active collection component for further processing such as lysis or direct amplification of the at least one nucleic acid. In other embodiments, the concentration step may be performed without performing an additional step of transferring the biological sample from the substrate that the sample was deposited upon. The concentration of the collected nucleic acid to a very small surface area permits direct PCR amplification in a very small volume which can provide increased sensitivity and simplified workflows. No additional manipulation of the collected nucleic acid may be needed, additionally preventing toss of limited amounts of the nucleic acids provided in the biological sample.

System. A system for collecting a biological sample comprising nucleic acid and at least one ridge and valley signature of an individual includes at least one imaging component to image the at least one ridge and valley signature of the individual and a substrate configured to collect the biological sample containing nucleic acid from the individual.

The biological sample containing nucleic acid is collected from the skin of the appendage of the individual. The skin is a complicated organ and includes more than one layer of cell and tissue type. The epidermis refers to the tissues on the surface of human or animal skin and includes materials secreted therefrom or derived from the lower layers of the skin, from which DNA can be easily obtained for use in identifying the individual. The outermost layer of the skin is the stratum corneum. Below the epidermis layer of the skin is the dermis layer containing fibroblasts, macrophages and adipocytes, three cell types each having a nucleus containing nucleic acid. In addition, the dermis has a vascular network of blood veins, arteries and lymph vessel containing white blood cells having a nucleus as does the erector pill muscle tissue, sebaceous glands and body fluids also present within the dermis. Additionally, sweat glands and vessels in the dermis may contain genetic materials in the form of intact ceils or as free DNA, which may be released up to the epidermis for collection by the systems and methods of the invention. Any or all of these nucleic acid containing materials are encompassed by the biological sample, in various embodiments of the invention, collecting the biological sample is non-invasive.

The system may collect simultaneously at least one ridge and valley signature of an individual and a biological sample containing nucleic acid or may collect in succession the signature and biological sample or, vice versa, the biological sample and the signature with an at least first imaging component. The methods of collection provide collection of both the biological sample and the at least one ridge and valley signature white the individual may touch only one apparatus. Additional motions or steps of touching additional platens or substrates may not be required to collect the biological sample and the at least one ridge and valley signature. The ridge refers to a friction ridge, the raised part of the epidermal layer of the skin of the fingers, toes, palm of the hand or sole of the foot and the valley being the depression in the epidermis between two adjacent ridges. The ridges and valleys are commonly referred to as fingerprints, palm prints, toe prints or footprints depending on the origin of the ridge and valley signature.

At least a first imaging component. In various embodiments, the system includes at least a first imaging component configured to obtain a ridge and valley signature of the individual. The imaging component may employ energy waves, such as light as described above, or other energy waves such as electromagnetic waves, capacitance, infra-red or sonic, e.g., ultrasound based components to provide an image of the ridge and valley signature. When the term imaging component is used in the context of capturing ridge and valley signatures, this includes any component that captures a digital or analog electronic representation of ridge and valley signatures.

Ridge and valley signatures may also be obtained using a touchless three-dimensional ridge and valley scanner using a digital processing means. (Wang, Yongchang; Q. Hao, A. Fatehpuria, D. L. Lau and L. G. Hassebrook (2009). "Data Acquisition and Quality Analysis of 3-Dimensional Fingerprints". Florida: IEEE conference on Biometrics, Identity and Security. http://vis.uky.edu/~realtime3d/Doc/3D_Fingerprint_Quality.pdf. Retrieved March 2010. Wang, Yongchang; D. L. Lau and L. G. Hassebrook (2010). "Fit-sphere unwrapping and performance analysis of 3D Fingerprints", Applied Optics, pp. 592-600).

In one embodiment of the present teachings, the system may include at least a first optical imaging component. In other embodiments, the system can include at least a first solid-state ridge and valley signature reader. The optical imaging component has an illuminating means for optically collecting the ridge and valley signature using an optical scanner as is known to one of skill in the art. The optical scanner can be an array of a plurality of light emitting diodes or a multispectral illuminator. The optical scanner may be a camera, an active pixel imager, a CMOS imager, an imager that images in multiple wavelengths, a CCD camera, a photo detector array, or a TFT imager, in an optical scanner a beam of light passes through scanning surface to illuminate the topological impression made by the appendage, including a finger, hand, palm, toe, sole or foot, when positioned against the scanning surface of the at least first imaging component.

Any suitable instrumentation may be used to acquire the image of an appendage according to the methods described herein. Some instruments and techniques include but are not limited to those disclosed in U.S. Pat. Nos. 4,537,484, 6,175,407, 6,665,427, 8,014,581, 8,036,431, 5,177,353, 6,282,303, 6,188,781, 6,741,729, 6,122,394, 6,826,000, 6,496,630, 6,628,813, 6,983,062, 7,162,060, 7,164,440, 7,657,067, 8,073,209, 7,130,817, 7,558,410, 7,565,541, 7,995,808, 7,899,217, 7,890,168, 7,835,554, 7,831,072, 7,819,311, 7,804,984, 7,801,339, 7,801,338, 7,751,594, 7,735,729, 7,668,350, 7,827,151, 7,620,212, 7,613,504, 7,545,963, 7,539,330, 7,508,965, 7,460,698, 7,440,597, 7,394,919, 7,388,152, 7,347,385, 7,263,213, 7,203,345, 7,147,153, 6,816,605, 6,628,809, 5,560,352, US20110235872, US20110211055, US20110185911, US20110183163, US20110085708, US20100248902, US20100087748, US20090245591, US20090148005, US20090092290, US20090080709, US20090048903, US20080304712, US20080298649, US20080297788, US20080232653, US20080192988, US20080025580, US20080025579, US20070116331, US20070030475, US20060274921, US20080244947, US20060210120, US20060202028, US20060110015, US20080082438, US20080002598, US20060002597, US20050271258, US20050285588, US20050285585, US20050205887, US20050185847, US20050007582, US20040240712, US20040047493, US20030223621, US20030078504, US20020183624, or US20020009213.

Scanning surface. The at least first imaging component comprises a scanning surface configured to permit the energy wave to penetrate the scanning surface, to image the at least one ridge and valley signature of an appendage of the individual positioned on at least a portion of the scanning surface. The scanning surface may be transparent or translucent to the energy wave used to image the at least one ridge and valley signature. The scanning surface may be formed from a material selected from a plastic, a polyolefin, a polystyrene, a metal, a metal alloy, a glass, a silicon or combinations thereof. In some embodiments, the surface comprises derivatized plastic, derivatized polyolefin, derivatized polystyrene, derivatized metal, derivatized metal ally, derivatized glass, derivatized silicon or combination of materials.

Substrate. The system provides a substrate configured to collect the biological sample from an appendage of the individual; wherein the scanning surface and the substrate are configured to permit collecting the at least one ridge and valley signature of the appendage. The system may provide non-invasive collection of the biological sample.

In FIG. 1A, a finger 101 rests on substrate 110 positioned above a scanning surface for the collection of a biological sample containing nucleic acid and a ridge and valley signature onto substrate 110-A. In some embodiments, the fingerprint containing the biological sample containing nucleic acid is deposited within a surface area 110-B-2, which may be about 20 mm wide.

In various embodiments, the substrate may comprise a polymeric film to collect the DNA sample from the appendage. In some embodiments, the polymeric film may be dimensionally stable enough to maintain structural integrity upon the scanning surface, in other embodiments, the polymeric film may be attached upon or to a support. Useful polymeric films include natural polymeric materials, which include but are not limited to starch, agarose, alginate, carrageenan or synthetic polymer gel, or a mixture thereof.

Synthetic polymers may also be used as the substrate. To form the polymeric film that may be used as a substrate, all types of polymerization, including cationic, anionic, copolymerization, chain copolymerization, cross-linking, uncrosslinked polymerization, and the like can be employed to synthesize the polymer gels forming part or all of the substrate. Essentially any type of polymer or copolymer formable from a fluid precursor, including but not limited to homopolymers, random copolymers, terblock polymers, radial polymers, linear polymers, branched polymers, and graft copolymers, can be incorporated onto the support as part or all of the substrate. An exemplary, non-limiting list of polymers that are suitable include cellulose polymers, including but not limited to hydroxyethylcellulose (HEC), hydroxypropyl methylcellulose (HPMC), hydroxypropyl cellulose (HPC); derivatives of sugars including but not limited to dextrans, mannitols, and gluco-pyranosides; pluronic copolymer liquid crystals; polyurethane; polyacids, including but not limited to lactic acids, and acrylic acids; polyamides; polyacrylamides, including but not limited to unsubstituted, N-substituted, and N,N-disubstituted acrylamides; polycarbonates; polyacetylenes; polydiacetylenes; polyphosphazenes; polysiloxane; polyolefins; polyesters; polyethers; poly(ether ketones); poly(alkylene oxides), including but not limited to polyethyleneoxides (PEO), polyethylethylene glycols (PEG) and polypropylene oxides (PPO); polyethylene terephthalate); poly(methyl methacrylate); polystyrene; substituted polystyrene, including but not limited to polystyrene sulfonates (PSS) and polyanetholes (PASA); poly(vinylpyrrolidones); proteinaceous material, and/or combinations and/or copolymers of the above.

In some embodiments, the polymeric film substrate may be selected from commercially available films, including but not limited to 3M PP2200, 3M PP2500, 3M CG600, or 3M CG3300. Many types of commercially available film may be suitable for use as a substrate, having no interference or substantially not interfering with the fingerprinting process. Suitable films have the ability to retain DNA on the film when the appendage of the individual contacts the film to image the ridge and valley signature. Some suitable films permit transfer of the biological sample containing the DNA, once collected, to another substrate. Other suitable films permit direct amplification of the DNA of the collected biological sample in the presence of the film. Yet other suitable films permit the at least one nucleic acid of the biological sample to be rinsed from the surface of the film, to be amplified thereafter.

In some embodiments, the polymeric film substrate has no modifications made to the polymeric film.

In other embodiments, the substrate may be made of glass, and may be made of any suitable glass material that will permit the energy wave to penetrate the substrate to image the ridge and valley signature of the appendage of the individual. Many types of commercially available glass may be suitable for use as a substrate, having no interference or substantially no interference with the fingerprinting process. Suitable glass has the ability to capture DNA on the glass when the appendage of the individual contacts the glass to image the ridge and valley signature. Some suitable glasses permit transfer of the biological sample containing the DNA, once collected, to another substrate. In some embodiments, a glass substrate will permit transfer of the at least one nucleic acid of the biological sample from the substrate while retaining other components of the biological sample. Other suitable glasses permit direct amplification of the DNA of the collected biological sample in the presence of the glass. Yet other suitable glasses permit the collected biological sample containing the DNA to be rinsed from the surface of the glass, to be amplified thereafter.

When an optical fingerprint scanner is used to image the at least one ridge and valley fingerprint, the substrate is translucent or transparent. In some embodiments, the substrate is substantially transparent to the energy wave.

In some embodiments, the substrate may be modified with chemically reactive groups to permit ionic, covalent or hydrogen bond interactions with species present within the biological sample. Suitable chemically reactive groups that may modify substrates include but are not limited to thiols, amines, carboxylic acids or the like, as is generally known in the art. Some examples of chemical modifications include, but are not limited to, amino groups including aliphatic and aromatic amines, carboxylic acids, aldehydes, amides, chloromethyl groups, hydrazide, hydroxyl groups, sulfonates and phosphates. These functional groups can be used to add any number of modifications to the polymeric or glass substrate, generally using known chemistries, including, but not limited to the use of amino-functionalized linkers, sulfhydryl linkers, etc. There are a number of sulfhydryl reactive linkers known in the art such as SPDP, maleimides, alpha-haloacetyls, and pyridyl disulfides. Similarly, amino groups on the polymeric or glass substrate can be attached using linkers; for example, a large number of stable bifunctional groups are well known in the art, including homobifunctional and heterobifunctional linkers. In an additional embodiment, carboxyl groups on the substrate can be derivatized using well-known linkers. For example, carbodiimides activate carboxyl groups for attack by good nucleophiles such as amines.

In some embodiments, the chemical modification of the substrate is performed to attach, covalently or noncovalently, a reagent, including but not limited to an enzyme, a binding partner, a surfactant, an anionic polymer or a zwitterionic species to assist in the collection of DNA from the subject. In some embodiments, the chemical modification may introduce electrically conductive polymers to the substrate, to assist in collection of DNA from the subject, if conductive polymers form part of the substrate, the system may further provide suitable electrical flow across the substrate to provide ionotophoretic assistance to drive charged nucleic acids from the appendage to the substrate, when the appendage is in contact with the substrate and the electrical circuit is completed.

In some embodiments, the polymeric film is modified to be adhesive. In other embodiments, the polymeric film is tackified, assisting in collection of the biological sample, without leading to physical handling difficulties.

In some embodiments of the invention, a support such as a glass slide or plastic sheet may be modified covalently to attach a polymeric substrate layer upon the support, thus incorporating one or more of the chemical modifications described above. In other embodiments, a polymeric layer forming a substrate is formed on the support without covalent attachment to the support.

In yet other embodiments, when a substrate is modified chemically to covalently attach one or more reagents, an enzyme, including but not limited to proteinase K may be attached to the substrate to assist in extracting nucleic acids from the appendage or from the biological sample once collected. In other embodiments, an enzyme is covalently attached to the substrate, and may be a proteinase selected from the group consisting of keratinase, papain, bromelain, and proteinase K. In other embodiments, the substrate is modified covalently to attach a charged polymer to assist in extracting nucleic acids from the appendage or from the biological sample once collected. In yet other embodiments, a surfactant is associated with the substrate noncovalently to assist in extracting nucleic acids from the appendage or from the biological sample once collected. In some embodiments, a zwitterionic species may be present in the substrate to assist in separating nucleic acids from other components of the cells collected. In some other embodiments, the substrate is chemically modified to covalently attach an antibody to a target moiety present on the skin of the appendage or in the collected biological sample, thus providing a binding partner to the target moiety. In some embodiments, wherein a binding partner is immobilized on the substrate, cleavage of the binding partner along with or separately from its binding target moiety may be performed.

Substrate Support. The system also may provide a support for the substrate. In some embodiments, the support may be configured to permit the collection of the at least one ridge and valley signature through the support and the substrate. In other embodiments, the support is configured to be located outside of the region imaged for the collection of the at least one ridge and valley signature.

The substrate support may be made of any material capable of forming a solid base. A suitable material for a substrate support may have any of a variety of properties depending upon the particular embodiments, including for example, porous, nonporous, rigid, elastic, pliable, malleable, low temperature melting, high temperature melting, and/or chemically resistant to one or more solvents commonly used in the reactions set forth herein. In some embodiments, the substrate support is formed from a material selected from a polymer, a metal, s metal alloy, a glass, a silicon material or combinations thereof. Suitable polymers include but are not limited to, plastic; polypropylene, polyethylene, polybutylene, polyurethane, nylon, polymer such as acrylic, acrylonitrile butadiene styrene (ABS), ULTEM (Polyetherimide), acetal copolymer, PROPYLUX HS (heat stabilized polypropylene), RADEL A (polyethersulfone), RADEL R (polyarylethersulfone), UDEL (polysulfone), NORYL PPO (polyphenylene oxide & styrene), Polycarbonate, UHMW-PE (ultra high molecular weight polyethylene), Polyetheretherketon (PEEK), polyphenylene sulfide (PPS, TECHTRON or RYTON), polyolefin or polystyrene; metal such as aluminum, iron, steel or an alloy; other materials such as glass or silicon, or derivatives or combinations of these or other suitable materials. In some of the embodiments of the present teachings, the substrate support is made of a material that is transparent or translucent.

In some embodiments, the substrate support is modified with chemically reactive groups to attach a substrate via ionic, covalent or hydrogen bonds. Chemically reactive groups include, but are not limited to thiols, amines, carboxylic acids, and the like. Some examples of chemical modifications include, but are not limited to, amino groups including aliphatic and aromatic amines, carboxylic acids, aldehydes, amides, chloromethyl groups, hydrazide, hydroxyl groups, sulfonates and phosphates. These functional groups can be used to add any number of modifications to the support, generally using known chemistries, including, but not limited to the use of amino-functionalized linkers, sulfhydryl linkers, etc. There are a number of sulfhydryl reactive linkers known in the art such as SPDP, maleimides, alpha-haloacetyls, and pyridyl disulfides. Similarly, amino groups on the substrate support can be attached using linkers; for example, a large number of stable bifunctional groups are well known in the art, including homobifunctional and heterobifunctional linkers. In an additional embodiment, carboxyl groups present on the support can be derivatized using well-known linkers. For example, carbodiimides activate carboxyl groups for attack by good nucleophiles such as amines.

The substrate support may be formed to underlay the entire substrate, underlay part of the substrate or be attached to the substrate. The substrate support may be formed to hold a liquid or non-rigid gel. It may be formed to fit around one or more fingers of a hand. The substrate support may be formed to fit into a depression upon the scanning surface of the at least one imaging component.

In some embodiments, a substrate support may contain a gel that can maintain its shape, a non-rigid gel or a liquid.

Substrate Frame. In some embodiments the substrate may further comprise a frame configured to support the substrate. The frame may be formed from a material selected from a plastic, a paper, a polyolefin, a polystyrene, a metal, a metal alloy, a glass, a silicon or combinations thereof. The substrate frame may further include a cover component configured to protect the surface of the substrate before and after collection of the ridge and valley signature and the biological sample.

Any of the substrate, substrate support, substrate frame or cover may have an identifier that associates the biological sample of the individual with the at least one ridge and valley signature obtained from the individual.

Sample concentration device. A sample concentration device, according to various aspects of the invention, includes an active collection component having a first surface area forming an active collection surface area and a handling component, where the active collection component is detachably connected to at least one of a first or second portion of the handling component; and where the device is configured to: a) collect a biological sample from at feast a first surface area of a substrate to the active collection surface area, where the active collection surface area is at least 50% smaller than the at least first surface area of the substrate; and b) permit an amplification reaction of nucleic acid of the biological sample concentrated on at least a first portion of the active collection surface area. In various embodiments, the sample may be not transferred from the at least first portion of the active collection surface area before being subjected to the amplification reaction of the nucleic acid contained within the biological sample.

Active collection component. The sample concentration device may be configured to detach the active collection component from at least one of a first or a second portion of the handling component to permit analysis of the sample. The active collection component may be attached to the first or the second portion of the handling component via adhesive that may be disrupted after sample collection. The active collection component may be attached to the handling component via securing elements on the second portion of the handling component which may be removed or released after sample collection. The securing elements may include, but are not limited to, clips, snaps, O-rings, other pressurized fittings, or adhesive that is removable. The active collection component may be detachable from the handling component by tearing one or more perforated junctions between the active collection component and the second portion of the handling component. In other embodiments, the active collection component may be connected to the first portion of the handling component by at least a second surface area of the active collection component. In some embodiments, the at least second surface area of the active collection component is a surface area on the opposite face of the active collection component from the active surface area.

In some embodiments, the active collection component is attached to the handling component via a pre-scored junction segment, wherein the pre-scored junction segment may be fractured to detach the active collection component from the second portion of the handling component. In some embodiments, when the active collection component is detached by fracturing the pre-scored junction segment, the first portion of the handling component remains with the active collection component. In other embodiments, the active collection component is attached to the handling component via friction, vacuum or static charge.

The active collection component may be shaped in a variety of configurations. One nonlimiting shape includes a strip shape. The active collection component may have different widths at various points along the strip shape, in order to provide either larger or smaller dimensions to the active collection surface area. In other embodiments, the active collection component may be formed in a disk, curved, or cupped shape. The active collection component may have a disk shaped active collection surface area.

The active collection component may be formed of a material configured to be compatible with reaction conditions of an analysis performed on the sample. The active collection component may be configured in a sheet form.

The active collection component may be formed from any suitable fibrous material. Suitable fibrous material includes natural fibers, synthetic polymeric fibers or a combination thereof.

The active collection component can be a paper material selected from Whatman(r) paper, including W-903 paper, FTA™ paper, FTA™ Elute paper, FTA™DMPK paper, Ahlstrom A-228 paper, M-TFN paper, FTA® paper, FP705™ paper, Bode DNA collection paper, nitrocellulose paper, nylon paper, cellulose paper, Dacron paper, cotton paper, and polyester papers, and combinations thereof.

In some embodiments, the active collection component may be an anion exchange membrane, (e.g., AMI-7001, available from Membranes international Inc., Ringwood, N.J.) In one non-limiting example, the anion exchange membrane may be made of polystyrene/divinyl benzene co-polymers that have been functionalized with quaternary amine groups. The functionalized membrane may attract nucleic acids, in other embodiments, an ion exchange membrane (Pall Corporation, Ann Arbor, Mich.) can be used for capturing a sample from a substrate. In certain embodiments the use of an anion exchange or cation exchange membrane, or more generally an ton exchange membrane, for capturing nucleic acid may operate in the presence of a lysis solution. Basically, the nucleic acid is separated from the substrate, to the positively charged quaternary amine groups of the membrane by displacing chloride ions. Following extraction of the nucleic acid, the membrane would be dried and a 0.8 mm to 1.5 mm punch taken for genotyping analysis.

Synthetic polymers may also be used as the active collection component. To form the polymeric film or fiber that may be used as an active collection component, all types of polymerization, including cationic, anionic, copolymerization, chain copolymerization, cross-linking, uncrosslinked polymerization, and the like can be employed to synthesize the polymer gels forming part or all of the active collection component. Essentially any type of polymer or copolymer formable from a fluid precursor, including but not limited to homopolymers, random copolymers, terblock polymers, radial polymers, linear polymers, branched polymers, and graft copolymers, can be incorporated onto the support as part of all of the substrate. An exemplary, non-limiting list of polymers that are suitable include cellulose polymers, including but not limited to hydroxyethylcellulose (HEC), hydroxypropyl methylcellulose (HPMC), hydroxypropyl cellulose (HPC); derivatives of sugars including but not limited to dextrans, mannitols, and gluco-pyranosides; pluronic copolymer liquid crystals; polyurethane; polyacids, including but not limited to lactic acids, and acrylic acids; polyamides; polyacrylamides, including but not limited to unsubstituted, N-substituted, and N,N-disubstituted acrylamides; polycarbonates; polyacetylenes; polydiacetylenes; polyphosphazenes; polysiloxane; polyolefins; polyesters; polyethers; poly(ether ketones); poly(alkylene oxides), including but not limited to polyethyleneoxides (PEO), polyethylethylene glycols (PEG) and polypropylene oxides (PPO); polyethylene terephthalate); poly(methyl methacrylate); polystyrene; substituted polystyrene, including but not limited to polystyrene sulfonates (PSS) and polyanetholes (PASA); polyvinylpyrrolidones); proteinaceous material, and/or combinations and/or copolymers of the above.

In some embodiments, the active collection component may be modified with chemically reactive groups to permit ionic, covalent or hydrogen bond interactions with nucleic acids present within the biological sample. Suitable chemically reactive groups that may modify an active collection component include but are not limited to thiols, amines, carboxylic acids or the like, as is generally known in the art. Some examples of chemical modifications include, but are not limited to, amino groups including aliphatic and aromatic amines, carboxylic acids, aldehydes, amides, chloromethyl groups, hydrazide, hydroxyl groups, sulfonates and phosphates. These functional groups can be used to add any number of modifications to the active collection component, generally using known chemistries, including, but not limited to the use of amino-functionalized linkers, sulfhydryl linkers, etc. There are a number of sulfhydryl reactive linkers known in the art such as SFDP, maleimides, alpha-haloacetyls, and pyridyl disulfides. Similarly, amino groups may be attached to the active collection component using linkers; for example, a large number of stable bifunctional groups are well known in the art, including homobifunctional and heterobifunctional linkers, in an additional embodiment, carboxyl groups on the active collection component can be derivatized using well-known linkers. For example, carbodiimides activate carboxyl groups for attack by good nucleophiles such as amines.

In some embodiments, the chemical modification of the active collection component is performed to attach, covalently or noncovalently, a reagent, including but not limited to an enzyme, a binding partner, a surfactant, an anionic polymer or a zwitterionic species to assist in the collection of the sample from the substrate. In some embodiments, the chemical modification may introduce electrically conductive polymers to the active collection component, to assist in collection of the nucleic acid from the substrate. If conductive polymers form part of the active collection component, the system may further provide suitable electrical flow across the active collection component to provide ionotophoretic assistance to drive charged nucleic acids from the substrate to the active collection component, when the electrical circuit is completed.

In yet other embodiments, when an active collection component is modified chemically to covalently attach one or more reagents, an enzyme, including but not limited to proteinase K may be attached to the active collection component to assist in extracting nucleic acids from the sample once collected. In other embodiments, an enzyme is covalently attached to the active collection component, and may be a proteinase selected from the group consisting of keratinase, papain, bromelain, and proteinase K. In other embodiments, the active collection component is modified covalently to attach a charged polymer to assist in extracting nucleic acids from the sample once collected. In yet other embodiments, a surfactant is associated with the active collection component noncovalently to assist in extracting nucleic acids from the sample once collected. In some embodiments, a zwitterionic species may be present in the active collection component to assist in separating nucleic acids from other components of the sample. In some other embodiments, the active collection component is chemically modified to covalently attach an antibody to a target moiety potentially present in the sample, thus providing a binding partner to the target moiety. In some embodiments, where a binding partner is immobilized on the active collection component, cleavage of the binding partner along with or separately from its binding target moiety may be performed.

In some embodiments, the polymeric active collection component has no modifications made to the fiber from which the polymeric active collection component is made.

Some embodiments of the active collection component permit transfer of the sample, once collected to the active collection component, to another receptacle or material for analysis of the sample. In some embodiments, the active collection component permits transfer of the sample via rinsing. In other embodiments, the active collection component permits transfer of the sample via alteration of its characteristics, such as electric charge, or release from a chemically modified film or fiber. Other suitable active collection components permit direct analysis of the sample, collected from the substrate, in the presence of the active collection component. In other embodiments, no transfer of the nucleic acids collected from the substrate is made before analysis of the nucleic acids, where analysis includes amplification of the nucleic acids and detection of the amplified nucleic acids.

Active collection surface area. The active collection surface area is configured to collect a sample from at least a first surface area of a substrate. The active collection surface area of the active collection component may be configured in a variety of configurations, and a person of skill can determine that the following descriptions are not meant to limit the number of possible configurations. The active collection surface area may have an oblong configuration, circular, or cupped shape.

In one embodiment, the active collection surface area is configured to be the surface area encompassing an exterior edge of an angled fold of the active collection component, where the angled fold is formed over a first portion of the handling component. In some embodiments, a length of the active collection component along the angled fold may be about 20 mm or less. The length of the active collection component along the angled fold may be about 10 mm or less. In other embodiments, the length of the active collection component along the angled fold may be about 5 mm or less. In some embodiments, the angled fold of the active collection component may form an acute angle, i.e., less than 90 degrees. In various embodiments of the active collection surface area encompassing an exterior edge of an angled fold of the active collection component, the width of the active surface area from the angled fold may be about 5 mm or less. In other embodiments, the width of the active collection surface area from the angled fold may be about 5 mm or less. In yet other embodiments, the width of the active collection surface area from the angled fold may be about 2 mm or less. Non-limiting examples of various active collection surface areas having an exterior edge of an angled fold of the active collection component are shown in FIGS. 2A-B, 3, 16A-B, 17, 18, and 19. In various embodiments, the exterior edge of the angled fold includes an angled fold that may be a rolled edge having a diameter of less than about 5 mm. In some embodiments, the exterior edge of the angled fold includes an angled fold that may include a rolled edge having a diameter of less than about 3 mm. One example of a rolled angled edge is shown in FIG. 19-2, where the exterior roiled angled fold is formed around a dowel shaped support having a diameter of 5 mm or less. In various embodiments, the active collection surface area may be formed along an edge that is curved or circular.

In various embodiments, the active collection surface area is smaller than the at least first surface area of a substrate from which a sample is collected, and concentrates a potentially limited amount of sample to the active collection surface area. In some embodiments, the active collection surface area is at least about 50% smaller than the at least first surface area of the substrate. In other embodiments, the active collection surface area is at least about 90% smaller than the at least first surface area of the substrate. In yet other embodiments, the active collection surface area is at least about 200% smaller than the at least first surface area of the substrate.

The active collection surface area is configured to permit analysis of the sample concentrated on at least a first portion of the active collection surface area. In some embodiments, the entire active collection surface area, containing at least some of the collected biological sample, is submitted to analysis. In some embodiments, the at least first portion of the active collection surface area may be one or more punches taken from the surface area encompassing the angled fold. The punches may be of any shape. In some embodiments, the at least first portion of the active collection surface area is configured to fit within a reaction volume of about 2 ul to about 100 ul. In other embodiments, the at least first portion of the active surface area is configured to fit within a reaction volume of about 2 ul to about 50 ul. In various embodiments, the active collection surface area is configured to provide at least a second portion of the active collection surface area for archiving.

Handling component. The sample concentration device is configured to include a handling component configured to support the active collection component and permit collection of the biological sample from the substrate. The handling component may include at least a first portion that supports the active collection component and may additionally include a second portion that provides a handle for ease of operation and, optionally, for providing force when contacting the substrate. In some embodiments, the handling component is configured to detach the active collection component from at least one of the first or the second portion of the handling component to permit analysis of the sample. The active collection component may be attached to the handling component via adhesive that may be disrupted after sample collection. The active collection component may be attached to the handling component via securing elements such as clips, snaps, O-rings, guideholes and pins, guiding loops or other pressurized fittings on either the first portion or the second portion of the handling component which may be removed or released after sample collection. In some embodiments, the securing elements may not attach the active collection component but may offer improved grip for the operator. In other embodiments, the active collection component may be connected to the first portion of the handling component by at least a second surface area of the active collection component. In some embodiments, the at least second surface area of the active collection component is a surface area on the opposite face of the active collection component from the active surface area.

In various embodiments, the active collection component is connected to the first portion of the handling component by a detachable connector component. In some embodiments, the active collection component is attached to the handling component via a pre-scored junction segment, wherein the pre-scored junction segment may be fractured to detach the active collection component from the second portion of the handling component. In other embodiments, the active collection component is attached to the first portion of the handling component via friction, vacuum or static charge.

In some embodiments, the first support portion of the handling component may be a stiffening support for the active collection component. The stiffening support for the active collection component may taper to a thin edge, to support and create the angled fold of the active collection component. The tapered edge of the stiffening support of the handling component may have thickness of about 5 mm or less. In other embodiments, the tapered edge of the stiffening support may have a thickness of about 3 mm or less. In some other embodiments, the tapered edge of the stiffening support of the handling component may have a thickness of about 0.9 mm or less. The tapered edge of the stiffening support may have a width of about 20 mm or less. In some embodiments, the tapered edge of the stiffening support may have a width of about 5 mm or less. The length of the handle portion may be about 20 mm. In some embodiments or may be selected to be of any convenient length for contacting the substrate with ease of operation. The stiffening handle portion may be the same material for both the first and the second portions of the handling component.

In another embodiment the stiffening support of the first portion of the handling component may be configured as a convex base, where the active collection component is formed over the convex base forming a convex shape that contacts the substrate.

The stiffening support of the handling component may be made of any material capable of forming a solid base. A suitable material for a support may have any of a variety of properties depending upon the particular embodiments, including for example, porous, nonporous, rigid, elastic, pliable, malleable, low temperature melting, high temperature melting, and/or chemically resistant to one or more solvents commonly used in the reactions set forth herein. In some embodiments, the support is formed from a material selected from a stiffened paper, a wood product, a polymer, a metal, a metal alloy, a glass, a silicon material or combinations thereof. Suitable polymers include but are not limited to, plastic; polypropylene, polyethylene, polybutylene, polyurethane, nylon, polymer such as acrylic, acrylonitrile butadiene styrene (ABS), ULTEM (Polyetherimide), acetal copolymer, PROPYLUX HS (heat stabilized polypropylene), RADEL A (polyethersulfone), RADEL R (polyarylethersulfone), UDEL (polysulfone), NORYL PPG (polyphenylene oxide & styrene), Polycarbonate, UHMW-PE (ultra high molecular weight polyethylene), Polyetheretherketone (PEEK), polyphenylene sulfide (PPS, TECHTRON or RYTON), polyolefin or polystyrene; metal such as aluminum, iron, steel or an alloy; other materials such as glass or silicon, or derivatives or combinations of these or other suitable materials.

The stiffening support of the handling component may be formed to underlay the entire active collection component, or underlay part of the active collection component.

Handling component Including further absorptive/transport features. In various embodiments, the first portion of the handling component includes one or more absorptive layers underlying the active collection component, and in particular, the active collection surface area. The one or more absorptive layers of the handling component underlying the active collection component may be configured to be detached from the active collection component after the sample is collected, and before the portion(s) of the active collection surface area are removed for analysis. The one or more absorptive layers of the handling component may include paper, polymer or desiccant materials. The one or more absorptive layers of the handling component may be thicker than that of the active collection component, thereby absorbing more fluid, and leaving larger biomolecules collected to the active collection surface area. An active collection surface area having a thinner layer may permit a greater number of punches selected from it to increase the amount of sample while still fitting within a reaction volume of the analysis.

In other embodiments, additional wicking behavior may be obtained by creating an active collection component having relatively thinner layer at the active collection surface area, and relatively thicker layer surrounding the active collection surface area. This may provide relatively higher concentration of a higher molecular weight species such as nucleic acid at the active collection surface area, and decreased amounts of smaller molecular weight species, which may be of lesser interest in this particular example.

The handling component may also include other transport features, including but not limited to a user operated vacuum source embedded within the handling component and underlying the active collection component. This may permit active aspiration of fluid from the active collection surface area and provide concentration of the sample on the active collection surface area. The handling component may also include an aerosol functionality that may deliver a precisely metered amount of a collection assistance liquid, such as water, ethanol or acetonitrile as the sample concentration device collects the biological sample from the substrate.

Process of manufacturing an edge swab. Edge swabs, as described here, may include a handling component and an active collection component, and may be manufactured in a number of ways. The handling component may be manufactured of plastic or cardboard, amongst other materials. If the handling component is made of a plastic, it may be 3D printed or it may be injection molded. Alternatively, the handling component may be made of wood, metal, or cardboard and shaped by laser cutting.

In various embodiments, the handling component has a first portion configured to be a support portion and a second portion configured to be a handle portion. The first support portion of the handling component may provide stiffening support for the active collection component. The stiffening support portion may be fabricated to taper to a thin edge, to support and create the angled fold of the active collection component. The tapered edge of the stiffening support of the handling component may be fabricated to have a thickness of about 5 mm or less. In other embodiments, the tapered edge of the stiffening support may be fabricated to have a thickness of about 3 mm or less. In some other embodiments, the tapered edge of the stiffening support of the handling component may be fabricated to have a thickness of about 0.9 mm or less. The tapered edge of the stiffening support may have a width of about 20 mm or less. In some embodiments, the tapered edge of the stiffening support may be fabricated to have a width of about 5 mm or less. The handle portion may have a length of about 20 mm or less, in other embodiments, the handle portion may have a length of about 100 nm or less. The other dimensions of the support portion of the handling component may be selected as appropriate for the particular use of the edge swab, to support the remainder of the active collection component at regions away from the angled fold while permitting the edge swab to easily contact the substrate.

In various embodiments, the second portion of the handling component may be fabricated to be a stiffening support for a handle for ease of collecting the sample from the substrate. The handling component may be manufactured in many different configurations, as shown in FIGS. 2A-B, 3, 16A-B, 17, 18, and 19. The length of the handle portion may be about 20 mm. In some embodiments or may be selected to be of any convenient length for contacting the substrate with ease of operation. The handle portion may be configured to have a different range of lengths and may also be configured to include additional attachments for installation and use of an edge swab in an automated instrument, where the automated instrument performs the action of concentrating the biological sample from the substrate to the active collection surface area of the active collection component.

The active collection component of the edge swab may be made of any suitable material as described above. It may be fabricated in a sheet form, and in some embodiments, the sheet is of uniform thickness. In other embodiments, it is fabricated with a variable thickness, and in particular, may be fabricated to be thin where it is supported by the tapered edge of the support portion of the handling component, which forms the angled fold of the edge swab, and thicker elsewhere to provide more wicking capability or strength as it is secured to at least one of the support or the handle portion. In some embodiments, the active collection component is fabricated from a paper such as a paper material selected from Whatman(r) paper, including W-903 paper, FTA™ paper, FTA™ Elute paper, FTA™DMPK paper, Ahlstrom A-226 paper, M-TFN paper, FTA™ paper, FP705™ paper, Bode DNA collection paper, nitrocellulose paper, nylon paper, cellulose paper, Dacron paper, cotton paper, and polyester papers, and combinations thereof. The material for the active collection component may be fabricated to be a strip shape and may be of uniform length and width. Alternatively, the material may be fabricated with a uniform width throughout its length, except at the region, the active collection surface area, that is supported by the tapered edge of the support portion of the handling component, where if may have a decreased width relative to the remainder of the active collection component. In some embodiments, the strip may be about 5 mm by about 80 mm. Alternatively, the strip may be about 20 mm by about 100 mm. In some embodiments, the active collection surface area is about 1 mm by about 5 mm wide.

The active collection component may be fabricated to be secured by securing elements such as O-rings at one or more locations along the handle portion of the handling component. The active collection component may be secured by securing elements including but not limited to clips, snaps, clamps, or other fittings on the handle portion or the support portion of the handling component, where the securing element holds a portion of the strip of the collection component in tension against the handling component. Alternatively, the active collection component may be fabricated with double sided tape securing it to the handling component. In another embodiment, the handle portion of the handling component may be fabricated to have a guide hole piercing the handle, where each of both ends of the strip of the active collection component is fabricated with a through-hole at each end. The edge swab is assembled by placing the active collection component in place over the tapered edge of the support portion and aligning the through-holes of the active collection component with the pierced hole in the handle portion and securing all three sections with a rod or pin. In yet another embodiment, the handle portion of the handling component includes guide loops thru which each end of the active collection component passes and is secured. The securing elements may also provide ease of operation during the collection of the sample.

The edge swab may be preassembled before use, or it may be supplied to an end user unassembled. The handling component may be made available in a kit to the end user separately from the active collection component.

In yet another aspect, the invention provides a process for manufacturing an edge swab, including the steps of fabricating a handling component including a support portion and a handle portion; fabricating an active collection component including an active collection surface area in a strip; placing the active collection surface area of the active collection component over the support portion to create an angled edge; and securing the active collection component to at least one of the support portion or the handle portion of the handling component. In some embodiments, the handling component is plastic, in some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the active collection component may be fabricated to have a uniform width. In other embodiments, the active collection component may be fabricated where the active collection surface area has a smaller width than the rest of the active collection component.

In another aspect, the invention provides a process for manufacturing a handling component including the steps of fabricating a support portion and a handle portion. In some embodiments, the support portion of the handling component is fabricated to taper to a thin edge. The support portion may be fabricated to taper to a thin edge having a width less than about 20 mm wide and having a thickness less than about 5 mm. In other embodiments, the support portion may be fabricated to taper to a thin edge having a width less than about 5 mm wide and a thickness of less than about 3 mm thick. The handle portion may be less than about 20 mm long. In some embodiments, the handling component is plastic.

Some non-limiting exemplary embodiments of the sample concentration device and its use are shown in the following paragraphs.

FIG. 2A shows one embodiment of an edge swab which is a sample concentration device as described here. This edge swab device has a handling component composed of a handle portion 204 and a support portion 202 and an active collection component 201 attached to the handle portion 204. The active collection component may be secured and then easily detached from the handle portion through various kinds of simple mechanical mechanism using a securing element 208, one non-limiting example being incorporation of a snap point near the end of the handle at 208. The support portion 202 underlays the active collection surface area 203 of the active collection component, and creates an angled fold. The active collection surface area 203 is the surface area encompassing the angled edge supported by support portion 202, which can collect and concentrate the sample containing a substance of interest to the small surface area of 203, which in this embodiment has a length of about 20 mm. FIG. 2B shows an enlargement of the active collection component showing the outer surface 201-B of the active collection material as it is configured around the angled shaft of the support portion 202-8 underlying the active collection surface area 203-B. In some embodiments the width of the active surface area is about 20 mm. The device of FIG. 2A may be swabbed with or without some pressure upon the collected biological sample within surface area 110-B-2 of FIG. 1B to concentrate the sample to the active surface area 203.

Figure 3:
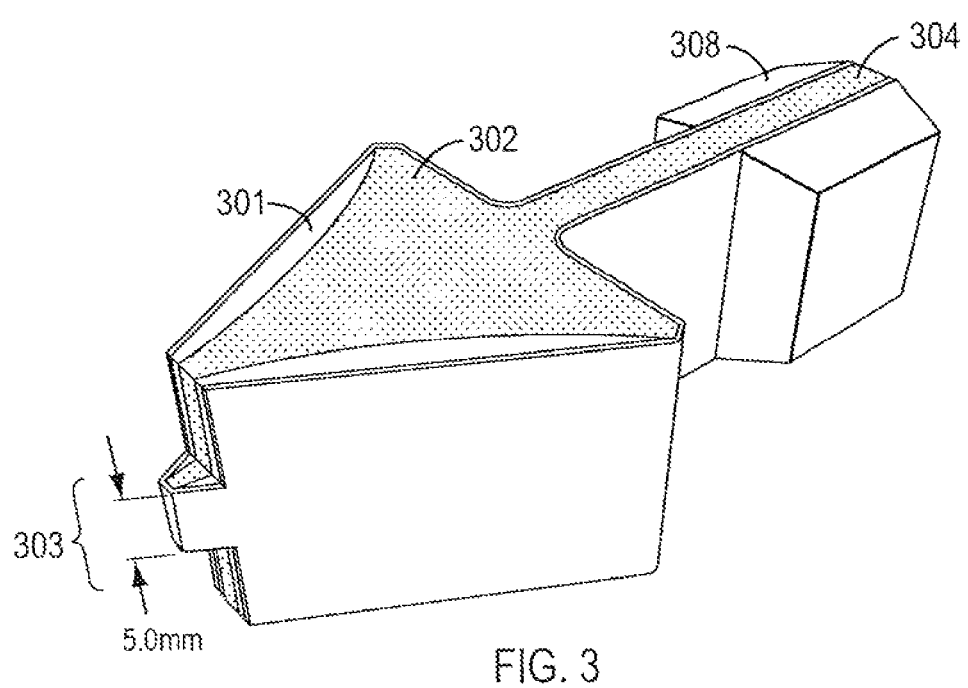
FIG. 3 is a graphical representation of another embodiment of an edge swab.

FIG. 3 shows another embodiment of a sample concentration device. The handling component is composed of a support portion 302 and a handle portion 304. The support portion 302 underlays and supports the active collection surface area 303 of the active collection component 301. The device has a very condensed active collection surface area 303 that contacts the sample on the substrate. The width of the active collection surface area of this embodiment is about 5 mm wide. In some embodiments, the handle portion 304 may be less than 2 cm long. At least one portion of the active collection surface area 303 is removed and used in an analysis. In some embodiments, securing elements 308 (only one marked) connect the active collection component detachably via snaps, clips, or other pressurizing elements that hold the active collection component against the handling component. In some embodiments, the at least one portion may be placed into the bottom of a well of a typical 96 well reaction plate and be submerged when using volumes of about 25 uL, which is a typical volumes, for example for a PCR reaction. In some embodiments, the at least one portion of the active collection surface area is configured to fit in the bottom of a typical 96 well reaction plate and be submerged when using volumes of about 2 ul to about 50 ul. The active collection component may be compatible with PCR reaction reagents and conditions.

The active collection component can be made of any material that enhances nucleic acid collection from the biological sample deposited within a fingerprint on transparency film or glass slide. Exemplary materials that may be used to make the active sample collection component include, but are not limited to Nylon® fibers, cotton fibers, Whatman filter paper or any other chemically treated paper suitable to enhance concentration of the sample from the substrate to the active collection component.

Figure 4:
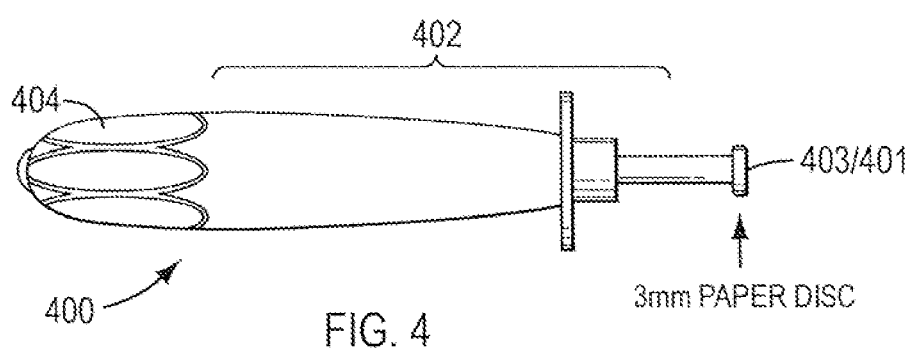
FIG. 4 is a graphical representation of another sample concentration device having a handle and an active collection component.

FIG. 4 shows another embodiment 400 of a sample concentration device. The handle portion 404 extends to a support portion 402 which underlays the active collection surface area 403 of the active collection component 401 which in this embodiment is a paper disc. The active collection component 401 is attached to the support 402 by exerting negative pressure via a suction mechanism within handle 404. The active surface area is swabbed with some pressure upon the collected biological sample within surface area 110-B-2 of FIG. 1B to concentrate the sample to the active surface area 403. Upon releasing the negative pressure the active collection surface area 403 is detached from the handling component for analysis.

Figure 5:
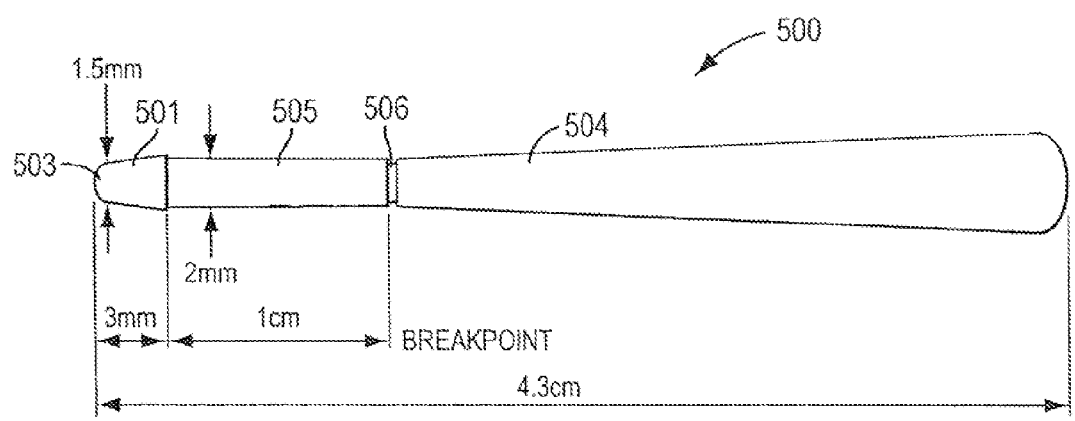
FIG. 5 is a graphical representation of another sample concentration device having a handle and an active collection component having an active surface are.

FIG. 5 shows yet another exemplary sample concentration device 500. The active surface area 503 of the active collection component 501 is swabbed with some pressure upon the collected biological sample within surface area 110-B-2 of FIG. 1B to concentrate the sample to the active surface area 503. The active collection surface area 503 may have a radius of as small as about 1.5 mm, and the active collection component 501 may have a length of about 5 mm. The active collection component may be connected via connector component 505 via a fracturable joint 508 to handle portion 504. In other embodiments, the joint 506 is not fracturable; the connector component is therefore connected directly to the handle 504. The size, shape and volume of the active collection component of the device may be configured so it may be placed into the bottom of a well of a typical 96 well reaction plate and be covered with anywhere from 2 ul to 25 ul reaction volume. The active collection component and shaft may be compatible with reaction reagents and conditions, for example, PCR reaction reagents and conditions. The active collection component 501 can be made of any material that enhances sample collection from the substrate. Exemplary materials that may be used to make the active sample collection component include, but are not limited to Nylon® fibers, cotton fibers, Whatman filter paper or any other chemically treated paper suitable to enhance concentration of the sample from the substrate to the active collection component. Therefore, in some embodiments, the invention provides a sample concentration device, having an active collection component entailing a first surface area configured to be an active collection surface area; and a handling component; where the active collection component is detachably connected to a second portion of the handling component; and where the device is configured to: a) collect a sample from at least a first surface area of a substrate to the active collection surface area; and b) permit analysis of the sample concentrated on at least a first portion of the active collection surface area.

Figure 16A:
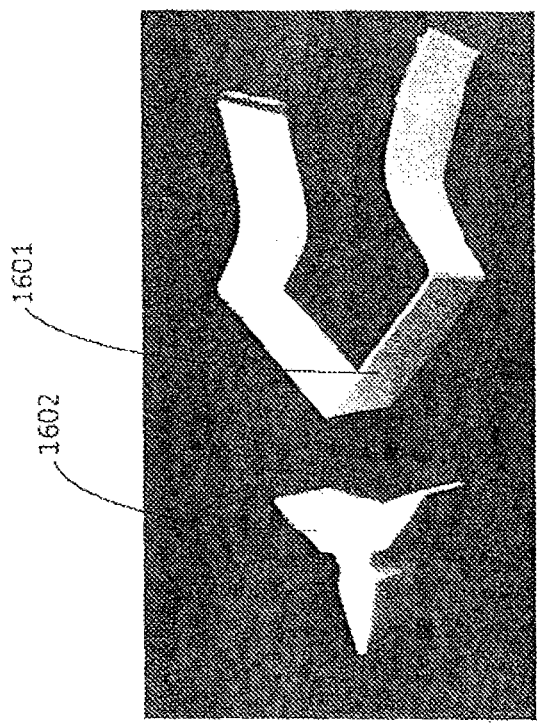
FIG. 16 shows (A) a graphical representation of the components and assembly of an edge swab, which is one example of a sample concentration device and (B) a graphical representation of the operation of the edge swab of FIG. 16A and retrieval of sample collected for analysis (C) and (D).
Figure 16B:
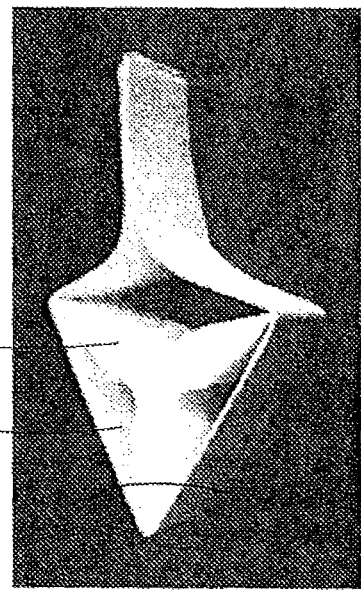
Figure 16D:
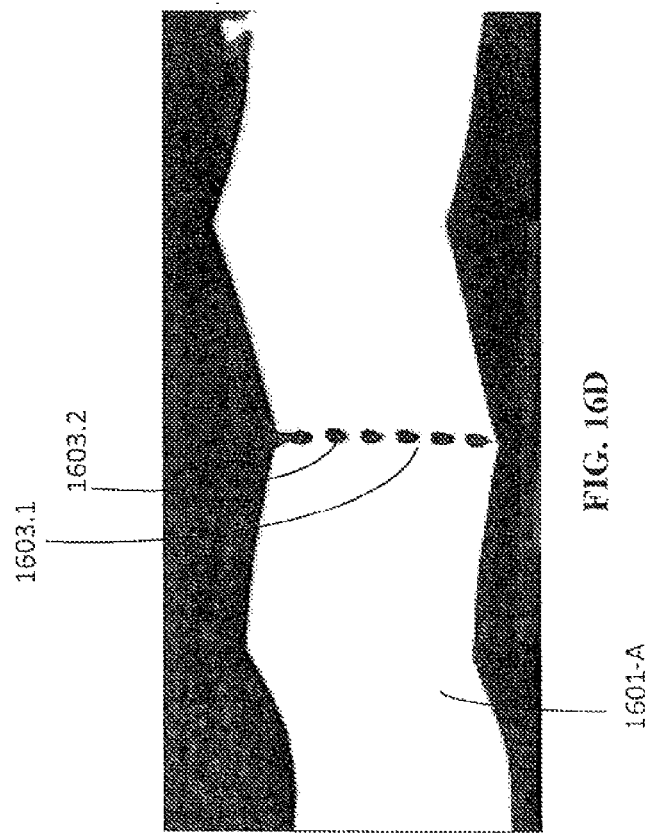
Figure 16C:
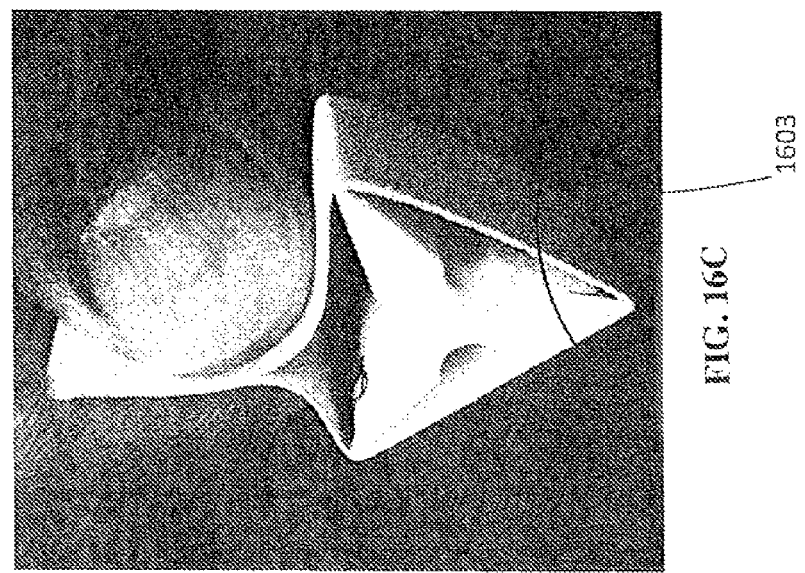

FIGS. 16A-D show various aspects of preparation and usage of an edge swab, which belongs to the class of the sample concentration devices described here. In FIG. 16A, the separate components of an edge swab is shown, where the handling component is represented by support element 1602, and the active collection component 1601 is shown, where the material forming the active collection component is a sheet and configured as a strip. In FIG. 16B, the assembled edge swab is shown where element 1603 represents the active collection surface area that contacts a substrate to collect a sample. The handling component support element 1602 is detachably connected to the active collection component by friction, and the support element underlays and supports the active collection component to form an angled fold having an exterior angled edge 1603. The outer surface 1601.1-2 of the active collection component 1601 has a portion of its surface area that is the active collection surface area, while the opposing side of the strip, 1601.2-2 detachably connects with the support element 1602. FIG. 16C shows an operator controlling the edge swab capable of exerting pressure, if needed, upon a substrate to collect a biological sample containing nucleic acids along the active collection surface area 1603 which encompasses the angled fold supported by handling component support element 1602. After the sample is collected, FIG. 16D shows the active collection component after detachment from the support element 1602, and further shows that at least one portion, punch 1603.1 has been selected from the active collection surface area 1603 and may be used directly in a PCR amplification, where another punch 1603.2 may also be used in the analysis or archived, and where the remainder of the active collection component 1601-A may also be retained for archiving.

FIG. 17 shows two other embodiments of an edge swab according to various aspects of the invention.

In FIG. 17A, one embodiment of an edge swab having a narrow strip of active collection component is shown, the outer surface of which 1701.1-1 is visible, which is attached to the handling component of the edge swab via clips, or other pressurized removable fittings at securing elements 1708.1-2 and 1708.2-2. The active collection surface area 1703-1 encompasses the angled fold and is about 5 mm wide. It is supported by a protruding section of the handling component support portion 1702-1 which is connected to handle portion 1704-1 of the handling component 1709-1.

In FIG. 17B, another embodiment of an edge swab is shown, it also has a narrow strip of active collection component at the active collection surface area 1703-2 encompassing the angled fold, and having a width of about 5 mm, but the active collection component broadens to form a wider active collection component (the outer surface 1701.1-2 and the inner surface 1701.2-2), which continues to a detachable connection at clip or friction fittings at securing elements 1708.1-2 and 1708.2-2 at the end of the handle portion 1704-2 of the handling component 1709-2, which has a support portion 1702-2 which underlays the angled fold and active collection surface area. The connection of the active collection component 1701.1-2 may also be effected by removable adhesive applied to the inner surface 1701.2-2 at a point along the handle portion 1704-2 or alternatively, the active collection component may be perforated where it meets securing elements 1708.1-2 and 1708.2-2.

FIG. 18 shows another embodiment of an edge swab. The components of the edge swab are shown after a sample has been collected, the active collection component has been detached from the handling component, and the portions of the active collection surface area have been selected out from the active collection component. The handling component 1809 is composed of two portions, the support portion 1802 and the handle portion 1804. As is shown in the figure, this support portion has a protruding segment 1802.1 of the support portion which provides the stiffening support for the active collection component 1801. The active collection component 1801 is shown after the sample has been collected, and the active collection component has been detached from both the support 1802 and the handle 1804 portions of the handling component 1809. Portions 1803.1 and 1803.2 have been removed from the active collection component, in particular from the active collection surface area encompassing the angled fold formed by the protruding 1802.1 portion of the support component 1802. The portions 1803.1 and 1803.2 of the active collection surface area may be used for analysis or for archiving.

FIG. 19A shows yet another embodiment of an edge swab. The handling component 1909-1 is composed of a support portion 1902-1 connected to a handle portion 1904-1. For this support component, the tapered edge of the support component has a width across the taper of about 0.9 mm to underlay and support the angled fold of the active collection component (having an outer surface 1901.1-1 that forms the exterior edge of the angled fold, and an inner surface 1901.2-1). The active collection surface area 1903-1 is the area encompassing the angled fold and is about 20 mm wide in this embodiment. The active collection component is detachably connected to the handling component either by friction created by securing elements 1908.1-1 and 1908.2-1 or with removable adhesive to any part of the handle portion 1904-1 of the handling component 1909-1.

FIG. 19B is an edge-on view of a rolled edge swab, where the angled fold is a semi-circular region formed around a rounded support component, not shown in this view. The diameter of the rolled angle is about 4 mm in this embodiment, and provides an active collection surface area encompassing this region 1903-2. The width of the active collection surface area is the dimension shown as 1903-2. The 4 mm region of 1903-2 can contact the substrate to collect sample along the width 1903-2.

Collection assistance liquid, in aspects of the invention, a collection assistance liquid may be present when a sample is concentrated to the active collection component. A collection assistance liquid may be a solvent, a detergent, or a lysis solution.

In some embodiments, a solvent may be added to the substrate or to the active collection component as the collection of the sample to the active collection component is performed.

Solvent. Some suitable solvents that may assist with collection of nucleic acids from the substrate may include water, ethanol or acetonitrile. In some embodiments, the presence of one of these solvents may help to collect more of the nucleic acids present within a fingerprint on a substrate. Additionally, the use of a solvent such as wafer, ethanol, or acetonitrile also provide a further concentrating effect as the biomolecule as well as small molecules such as salts are collected to the active collection surface area. If a solvent is present, the smaller molecules may be further transported out of the at least first portion of the active collection surface area, while the larger biomolecule is retained within the at least first portion of the active collection surface area.

As used here, the term "detergent" is any substance that reduces the surface tension of water, and is used synonymously with the term "surfactant". In certain embodiments, the detergent can be a cationic detergent, anionic detergent, nonionic detergent, or a zwitterionic detergent. Examples of nonionic detergents include triton, such as the Triton™ X series (Triton™ X-100 t-Oct-$C_6H_4$—$(OCH_2$—$CH_2)_x$OH, x=9-10, Triton™X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucyopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl) dimethylammonio]-1-propanesulf-onate. It is contemplated also that urea may be added with or without another detergent or surfactant.

In some embodiments, a surfactant that substantially lacks fluorescence between 300 nm and 750 nm is used in the methods of the invention. In some embodiments provided herein, the lysis solution comprises a surfactant at a concentration that has low or no emission at the emission wavelengths of dyes or labels commonly used for detecting RNA, DNA, or proteins when in use for in situ analysis of DNA, RNA, proteins or a surrogate thereof.

In some embodiments, an effective concentration of surfactant in a lysis mixture is a concentration of surfactant at which a sample is considered fully lysed as determined by propidium iodide staining using 1% TRITON X-100™ surfactant as a control Lysis-effective concentrations of exemplary surfactants range from 0.02% or 0.05%, to 3% or more for TRITON X-114™ surfactant, from 0.1% to 5% or more for NP-40™ surfactant, and from 0.05% to 1% or to 3% for TRITON X-100™ surfactant. When a combination of surfactants is used, the concentration of each surfactant may be lowered from the cited amounts.

The lysis solution may contain an enzyme to facilitate concentration of nucleic acids onto an active collection component, in certain embodiments, the lysis solution contains proteinase K. In various embodiments, proteinase K may be present in the lysis solution at about 0.8 mg/ml to about 1.5 mg/ml. In certain other embodiments the lysis solution can contain a protease enzyme. The enzyme may degrade structural proteins in order to permit extraction of biomolecules from biological cells on the substrate. The enzyme may be applied to the substrate while collection of the sample is performed, or the enzyme may be incorporated Into the active collection component, such as incorporation into a gel film, or paper. In certain embodiments herein, the lysis solution comprises a polypeptide having protease activity such as for example, proteinase K.

In lieu of, or in addition to, proteinase K, the lysis solution can comprise a serine protease such as trypsin, chymotrypsin, elastase, subtilisin, streptogrisin, thermitase, aqualysin, plasmin, cucumisin, or carboxypeptidase A, D, C, or Y; a cysteine protease such as papain, calpain, or clostripain; an acid protease such as pepsin, chymosin, or cathepsin; or a metalloprotease such as pronase, thermolysin, collegenase, dispase, an aminopeptidase or carboxypeptidase A, B, E/H, M, T, or U, Qiagen Protease (p/n 19155, Qiagen, Valencia, Calif.) is an alternative to proteinase K and can be inactivated by EDTA.

In other embodiments, the enzyme contained in the lysis solution is a pancreatic proteolytic enzyme, such as porcine pancreatic enzyme. Keratinases, that may have utility in collection of nucleic acids, include but are not limited to keratinases isolated from bacteria or fungi. Some keratinases have enhanced stabilities in the presence of detergents, surfactant, metal ions and solvents, which is useful for the methods of the present teachings. Some nonlimiting examples of a keratinase useful in the methods of the present teachings include the keratinases from *P. pastoris, B. megaterium*, and *B. licheniformis*.

In other embodiments, the lysis solution may include a surfactant to assist collection of the sample from the substrate or to assist in extracting a substance of interest from the sample once collected.

Sample concentration device: automatic operation. In some embodiments, the sample concentration device is supported operably within a housing of an apparatus which is configured to automatically concentrate a biological sample containing nucleic acid to a smaller surface area suitable for further processing, analysis, and optionally, storage. The housing may have a platform to secure the substrate containing the collected biological sample. Once the substrate is secured, the apparatus may initiate concentration of the biological sample to the active collection component. The apparatus may further add an identifier to the sample concentration device, which may identify the device as a whole or may identify the active collection component only. The identifier may be the identifier issued to the substrate when the ridge and valley signature and the biological sample was collected or it may contain additional information about the shipping, archiving or processing of the substrate after collection. The apparatus may comprise a processor which is configured to control the apparatus to concentrate the sample. The processor may be configured to add the identifier issued to the substrate and it may further be configured to add any additional information about the shipping, archiving or processing of the substrate after the collection process. The apparatus may also be provided with computer readable media to instruct the apparatus to perform the operations of concentration and identification. The computer readable medium may be non-transitory.

Additional imaging components. In another embodiment of the present teachings, the system can further comprise at least a second imaging component for collecting a second image of the individual. The second image of the individual can be either the face of the individual or a component of the individual amenable to biometric identification. Suitable biometric images that may be collected as the second image include a retinal scan, or iris scan, the contours of the ear, facial recognition, hand geometry, foot geometry, voice, odor and scent.

Various exemplary embodiments of the system and methods of use are described herein, but the invention is not limited by the particular embodiments, in any of these embodiments, a substrate with or without supports and/or a sample concentration device and/or an active collection component may be processed immediately in a further analysis or reaction, archived for future use, or shipped to another facility for processing or analysis. The image of the at least one ridge and valley signature may be sent to a database having a plurality of ridge and valley signatures as well as other physical biometric data. Each of the substrate, support, sample concentration device, active collection component, and at least one ridge and valley signature may have an identifier assigned in order to associate the collected biological sample and the at least one ridge and valley signature with the individual.

In various embodiments, the system collects at least one ridge and valley signature of an individual and a biological sample containing nucleic acid simultaneously or collects in succession the signature and biological sample or, vice versa, the biological sample and the signature with the at least first imaging system, while requiring the individual to touch an apparatus only once.

Processor. After collection of the at least one ridge and valley signature, the signature, in analog or digital format, can be transmitted to a database having a plurality of ridge and valley signatures, as well as any other physical biometric data collected and deemed suitable to transmission. In some embodiments, the system includes a processor configured to transmit the ridge and valley signature obtained from the individual to at least one database which retains ridge and valley signatures of individuals. In some embodiments the database is selected from the group consisting of a forensic, criminal, identity, child identity, missing persons, immigration, department of motor vehicles, terrorist, paternity, arrestee, convict database, access control or any combination thereof.

Identifier. In still other embodiments of the present teachings, the system can further comprise an identifier for associating identifying information with the signature, biological sample, and, optionally a physical image, including any of a facial image, an iris image, a retinal image or an ear image of the individual. In some embodiments, the name of the individual is included in the identifier. The identifier may aid in correlating various collected samples and may preclude sample mix-up and human error as may occur with nonsystematic sample labeling for identifying collected data and samples. In various embodiments, the identifier is alphanumeric, graphical, magnetic, or electromagnetic. In some embodiments, the identifier is a barcode. In various embodiments, the substrate comprises an identifier. In other embodiments, a support comprises an identifier. In yet other embodiments, both the substrate and the support comprise the identifier to aid in correlating the collected sample and images. In other embodiments, the sample concentration device includes an identifier, which may be provided on the active collection component, and/or the handling component. In some other embodiments, both the substrate and the support comprise an identifier to aid in correlating the collected sample and images. If more than one imaging component is included in the system, the same identifier may be used on all the collected data and samples of one individual.

Other components. In yet other embodiments, the system additionally includes amplification, purification and separation components which may be used to: obtain the at least one nucleic acid from the biological sample; purify the at least one nucleic acid before further amplification and analysis; amplify the at least one nucleic acid; separate the amplified at least one nucleic acid; and detect the amplified at least one nucleic acid. Any or ail of these additional components may be used to identify the individual. The biological sample containing at least one nucleic acid may be subjected to subsequent analysis for nucleic acid markers such as DNA markers for STRs, Indels, SNPs and combinations thereof as well as DNA sequencing methods. Reagents for analyzing nucleic acids are commercially available and include such reagents as the AmpF/STR® Identifiler® Direct PCR Amplification Kit (Applied Biosystems, Foster City, Calif.) or the PowerPlex® 18D System (Promega Corp. Madison, Wis.), which may be used in conjunction with Prep-n-Go™ Buffer (Applied Biosystems) following the manufacturer's instructions.

Kits. The invention also provides for kits. A kit may include any of the sample, concentration devices described here in any combination, and optionally, instructions for its use. The kit may further contain one or more of any of the various substrates described herein, where the substrate may or may not include a support. The kit may further include a collection assistance liquid, including but not limited to a solvent, a detergent or a lysis solution. The kit may further include reagents for stabilizing the sample on the active collection component for archiving or shipping. The kit may further include reagents for analysis of the sample, including but not limited to antibodies, stains, indicators, agar plates, or nucleic acid amplification reagents. The kit may contain other reagents for reactions such as PCR amplification reactions or analyses such as STR, SNP or Indel analyses. The kit may contain one or more proteases for extraction of the at least one nucleic acid from the biological sample collected to the active collection component.

The kit may include storage enclosures for the substrate and/or sample concentration device containing the biological sample and/or the nucleic acid, and may also contain directions for archiving. The kit may further include mailing enclosures for the substrate and/or active collection component or sample concentration device containing the biological sample or nucleic acid.

The enclosure included in a kit may include a frame to prevent contamination of any portion of the active collection component or the substrate. Any portion of the at least one enclosure may include an identifier to associate any of the portions of the active collection component with the substrate from which the sample was obtained. The identifier may further associate the substrate, the active collection component, or both with the individual providing the sample. In various embodiments, the identifier is alphanumeric, graphical, magnetic, or electromagnetic. In some embodiments, the identifier is a barcode.

In some embodiments, the kit may include instructions for use of the substrate and/or the sample concentration device, storage of the substrate, sample concentration device, or the active collection component after collection of the sample, processing of the substrate to concentrate the sample to the active collection component of the sample concentration device, and for relaying the image of the at least one ridge and valley signature to a database. The kit may include instructions for mailing the substrate, sample concentration device, or the active collection component after collection of the sample to another facility for analysis or archiving.

In a further aspect, the invention provides a kit including a handling component including a support portion and a handle portion, where the handling component is configured to support an active collection component for collection of a sample, and optionally, instructions for use. In some embodiments, the support portion of the handling component tapers to a thin edge. The support portion may taper to a thin edge having a width less than about 20 mm wide and having a thickness less than about 5 mm. In other embodiments, the support portion may taper to a thin edge having a width less than about 5 mm wide and a thickness of less than about 3 mm thick. The handle portion may be less than about 20 mm long. In some embodiments, the handling component is plastic. In some embodiments, the kit further includes one or more active collection components. The active collection component may include an active collection surface area. In some embodiments, the active collection component is a paper material selected from Whatman® paper, including W-903 paper, FTA™ paper, FTA™ Elute paper, FTA™DMPK paper, Ahlstrom A-226 paper, M-TFN paper, FTA™ paper, FP705™ paper, Bode DNA collection paper, nitrocellulose paper, nylon paper, cellulose paper, Dacron paper, cotton paper, and polyester papers, and combinations thereof. The material for the active collection component may have a strip shape and may be of uniform width along its length. Alternatively, the material may be fabricated with a uniform width throughout its length, except at the active collection surface area supported by the tapered edge of the support portion of the handling component, where it may have a decreased width relative to the remainder of the active collection component. The kit may further include removable attachments to attach the active collection component to the handling component, selected from the group of O-rings, snaps, clips, guideholes and securing pins, and double sided tape.

Methods

The invention provides for methods of collecting a biological sample comprising nucleic acid and at least one ridge and valley signature of an individual. In some embodiments, the methods include identifying the individual. In various embodiments, the method for collection of a biological sample comprising at least one nucleic acid and at least one ridge and valley signature of an individual includes providing at least a first imaging component. The at least one imaging component is configured to provide an energy wave and comprises a scanning surface configured to permit the energy wave to penetrate the scanning surface. The method includes providing a substrate configured to collect the biological sample from an appendage of the individual and configured to permit the energy wave to penetrate the scanning surface, where the substrate is positioned over the scanning surface. The method includes the steps of positioning the appendage of the individual upon the substrate, thereby depositing the biological sample upon the substrate; collecting the at least one ridge and valley signature from the appendage imaged by the energy wave; and concentrating the biological sample from the substrate to a sample concentration device. The sample concentration device may be any suitable sample concentration device described here.

Both the fingerprint and the biological sample may be provided to be of sufficient quality/quantity to identify the individual. The image of the fingerprint obtained by scanning through the substrate may be provided in high quality. When the image of the fingerprint is processed according to the requirements of any organization holding a database for reference, the digitized fingerprint may meet the threshold requirement. As may be seen in Example I, and particularly in FIG. 6, acquiring a fingerprint according to the methods described here, fingerprints scored at the highest level, NIST quality score I, may be obtained. Therefore, a fingerprint image of high quality is provided which may be processed electronically in any suitable fashion, to assign minutiae or other categorizing characteristics, and be suitable for transmission to any agency for database comparison or for storage in a database. One non-limiting example is the Integrated Automated Fingerprint Identification System (IAFIS) which is maintained by the Federal Bureau of Investigation, a United States government agency.

In some embodiments, the at least first imaging component is an optical scanner, where the optical scanner comprises a LED, laser diode, incandescent light source, or a multispectral imager. The at least first imaging component may alternatively be a camera, an active pixel imager, a CMOS imager, an imager that images in multiple wavelengths, a CCD camera, a photo detector array, and a TFT imager. The at least one ridge and valley signature may be collected electronically. The scanning surface of the at least first imaging component may be formed from a material selected from a plastic, a polyolefin, a polystyrene, a metal, a metal alloy, a glass, a silicon or combinations thereof. In some embodiments, the material of the scanning surface is transparent or translucent.

For the acquisition of nucleic acids of sufficient quantity and quality from a fingerprint, several factors may need to be addressed. To ensure sufficient quantity, an individual may be instructed to touch a portion of his face one or several times with the finger to be imaged prior to firmly pressing that finger on a substrate placed over the scanning portion of fingerprint imagins system. This may not be necessary in some embodiments of the method. The substrate useful in the method may be polymeric film or glass. In some embodiments, the polymeric film substrate may be a synthetic polymeric film. In other embodiments, the polymeric film substrate may be a natural polymer, including but not limited starch, an agarose, an alginate, a carrageenan, and the like, in some embodiments, the polymeric film substrate may be non-adhesive. In various embodiments, the substrate may be transparent or translucent.

Another aspect is obtaining high quality STR profiles from the nucleic acids deposited at the same time as a fingerprint, in some scenarios, a complicating effect is seen with other substances present in the deposited biological sample. While commercially available direct amplification STR chemistries are optimized to handle biological samples that may contain indigo, hematin and humic acid, all of which are inhibitors of the PCR amplification process, no system is optimized for the types of inhibitors possibly present in the biological samples acquired from a fingerprint deposition. Depending on the specific donor and the physiological condition of the skin of the individual at the time of fingerprinting, different amounts of sebum and sweat may be present. Sebum is produced by sebaceous glands and contain wax monoesters (approx. 25%), triglycerides (approx. 40%), free fatty acids (approx. 15%) and squalene (approx 10-15%). Sweat includes salts, urea, sugar and ammonia. Further, materials such as cosmetics, hair products, and sunscreens may be present when an individual deposits a fingerprint image containing a biological sample. Some or all of these chemicals may contribute to PCR inhibition. The normal skin pH of about 5.4 may also impact PCR efficiency under direct amplification workflows. Adjustment of the PCR master mixture composition may reduce the inhibiting effects of any of these materials. Evaluating a number of master mix/buffers, both commercially available buffers as well as other combinations, it has been discovered that the Global Filer(r) master mix provides the most robust results. This particular master mix provides a higher concentration of one or more polymerases as well as an increased percentage of bovine serum albumin (BSA). Both of these master mix components assist in overcoming inhibitors found in DNA samples acquired from fingerprints. It has been surprisingly found that use of the sample concentration swab to concentrate the sample and direct amplification as described here can combine to provide high quality STR analyses from the highly limited amount of nucleic acids deposited within a fingerprint, even with interference from other substances also present. As can be seen in Examples 1-9 and the accompanying FIGS. 7 to 15, the electropherograms can definitively identify the individual supplying the nucleic acids.

Methods for collection of the biological sample are described which include providing a sample concentration device which includes an active collection component having a first surface area configured to be an active collection surface area; and a handling component. The device is configured to: a) collect a sample from at feast a first surface area of a substrate to the active collection surface area; and b) permit analysis of the sample concentrated on at least a first portion of the active collection surface area. The active collection component is detachably connected to at least one of a first or a second portion of the handling component. To collect the sample, a substrate containing a biological sample (i.e., the substrate containing the biological sample after the fingerprint is deposited) is provided; and the sample is collected by contacting an active collection surface area of the active collection component of the sample concentration device to at least a first surface area of the substrate, thereby concentrating the sample to the active collection surface area. The method may further include the step of detaching the active collection component from at least one of the first or the second portion of the handling component of the sample concentration device. In some embodiments, the active collection component is detached from both the first and the second portion of the handling component. The method may further include the step of separating at least a first portion of the active collection surface area from the active collection component of the device.

The method for collection of the sample may further include the step of providing an identifier to associate the sample collected to the active collection surface area of the active collection component with the substrate from which the sample was collected, where the identifier is alphanumeric, graphical, magnetic, or electromagnetic. The identifier may be a barcode. The identifier may further associate the substrate and/or active collection surface area and/or active collection component with the individual depositing the biological sample and/or the fingerprint image obtained from the individual. The method may further include the step of shipping the sample concentration device including the sample to another location for archiving or testing. In other embodiments, the method may further include the step of shipping the active collection component including the sample to another location for archiving or testing.

In some embodiments the method may also include the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier to associate the biological sample of the individual with the at least one ridge and valley signature of the individual, wherein the identifier is alphanumeric, graphical, magnetic, or electromagnetic. The identifier may be a barcode.

The method may further include shipping the substrate containing the biological sample to another location for archiving or testing prior to the step of concentrating the biological sample.

The method may further include the step of archiving the substrate containing the biological sample prior to the step of concentrating the biological sample.

The method may further include the step of subjecting the biological sample to at least one of a polymerase chain reaction, a DNA sequencing reaction, STR analysis, SNP analysis, or Indel analysis after the sample has been concentrated to the sample concentration device.

Another method provided here is a method for identifying an individual, comprising the steps of: providing a sample concentration device which includes an active collection component having a first surface area configured to be an active collection surface area; a handling component; where the active collection component is detachably connected to at least one of a first or a second portion of the handling component; and where the device is configured to: a) collect the sample from at least a first surface area of a substrate to the active collection surface area; and b) permit analysis of the sample concentrated on at least a first portion of the active collection surface area; providing a substrate comprising a sample; and collecting the sample by contacting an active collection surface area of an active collection component of the sample concentration device to at least a first surface area of the substrate; and subjecting the sample to an analysis thereby providing identification of the individual. In various embodiments, the method for identifying an individual includes providing at least a first imaging component. The at least one imaging component is configured to provide an energy wave and comprises a scanning surface configured to permit the energy wave to penetrate the scanning surface. The method includes providing a substrate configured to collect the biological sample from an appendage of the individual and configured to permit the energy wave to penetrate the scanning surface, where the substrate is positioned over the scanning surface. The method includes the steps of positioning the appendage of the individual upon the substrate, thereby depositing the biological sample upon the substrate; collecting the at least one ridge and valley signature from the appendage imaged by the energy wave; and concentrating the biological sample from the substrate to a sample concentration device. The sample concentration device may be any suitable sample concentration device described here.

In various embodiments, the analysis may be at least one of a polymerase chain reaction, a DNA sequencing reaction, STR analysis, SNP analysis, or Indel analysis.

In some embodiments of the method for identification of an individual, the method may further include the step of detaching the active collection component from at least one of the first or the second portion of the handling component of the sample concentration device. The method may further include the step of separating at least a first portion of the active collection surface area from the active collection component. The method may further include the step of providing an identifier to associate the sample collected to the active collection surface area with the substrate from which the sample was collected, where the identifier is alphanumeric, graphical, magnetic, or electromagnetic. The identifier may be a barcode. The identifier may further associate the substrate and/or active collection surface area and/or active collection component with the individual depositing the biological sample and/or the fingerprint image obtained from the individual.

In various embodiments of the method for identification of an individual, the method may further include the step of shipping the sample concentration device including the sample to another location for archiving or testing. In other embodiments, the method may further include the step of shipping the active collection component including the sample to another location for archiving or testing.

In various embodiments of the method for identification of the substance of interest, the method may further include the step of sending the identity of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

Those having ordinary skill in the art will understand that many modifications, alternatives, and equivalents are possible. All such modifications, alternatives, and equivalents are intended to be encompassed herein.

EXAMPLES

The following procedures are representative of procedures that can be employed for the collection, analysis and archiving/cataloging biological samples and biometric data from an individual.

Example 1

Figure 6:
FIG. 6 is a graphical representation of a fingerprint image obtained from an individual according to the systems and methods of the invention.
Figure 7:
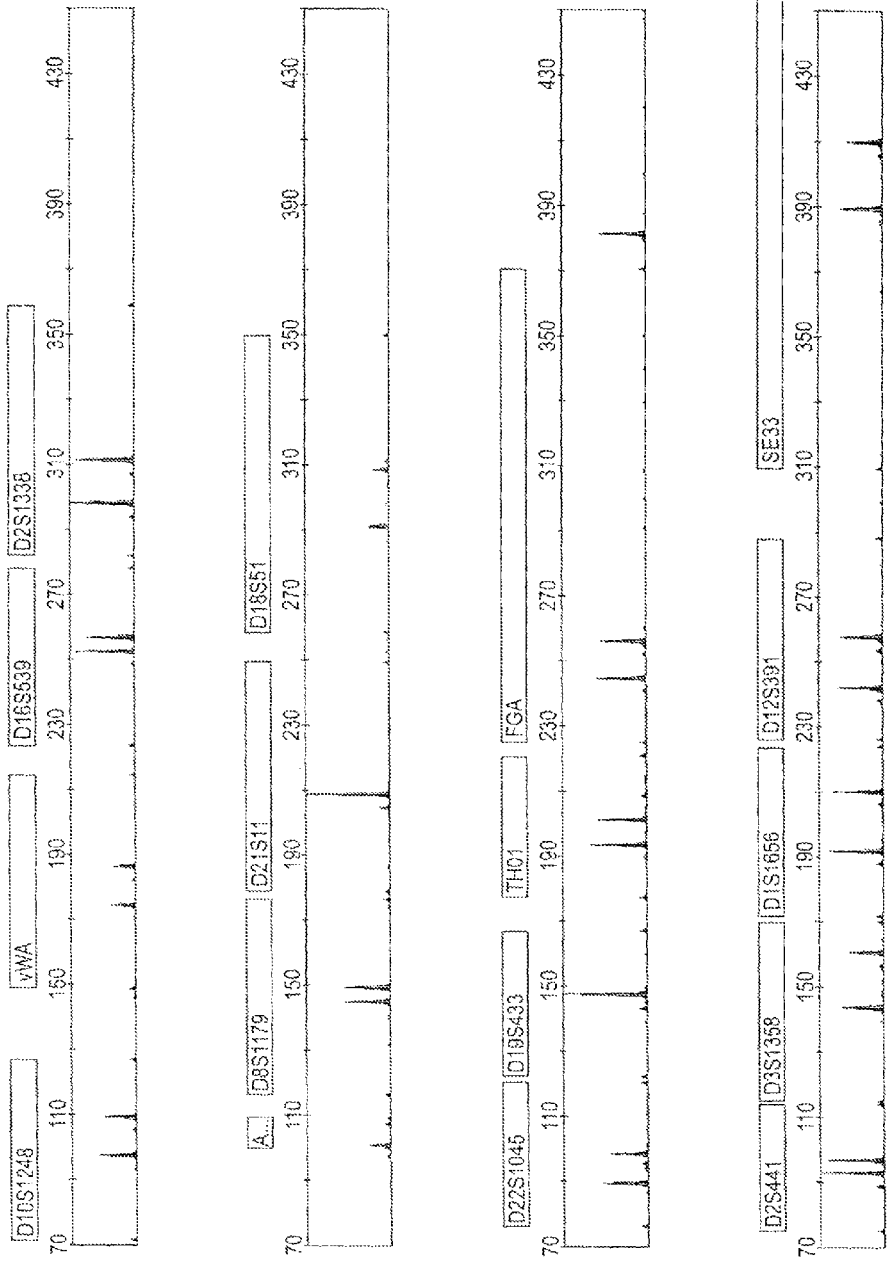
FIG. 7 is a graphical representation of a STR analysis obtained from an individual according to the systems and methods of the invention.
Figure 8:
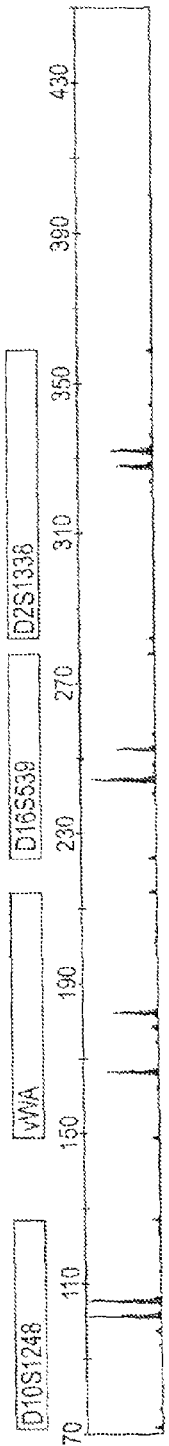
FIG. 8 is a graphical representation of a STR analysis obtained from an individual according to the systems and methods of the invention.
Figure 8:
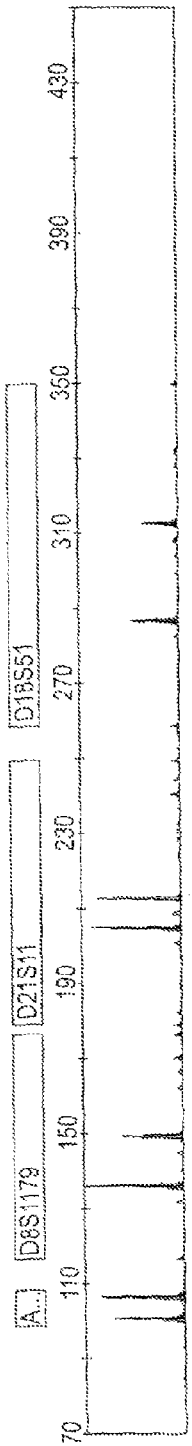
Figure 8:
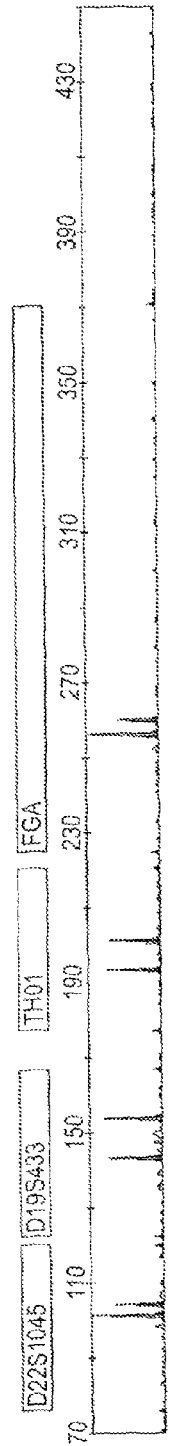
Figure 8:
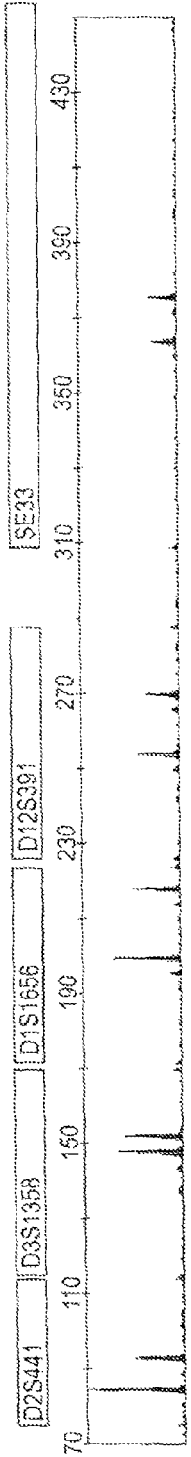
Figure 9:
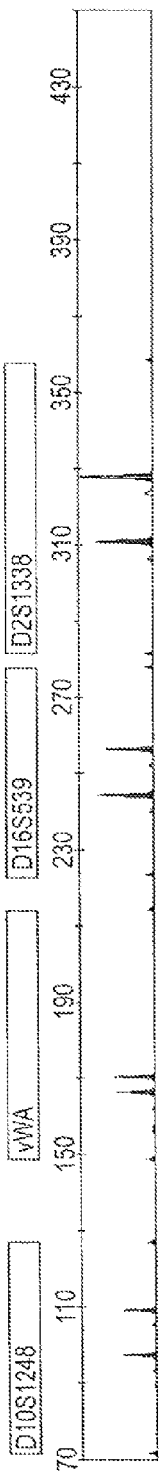
FIG. 9 is a graphical representation of a STR analysis obtained from an individual according to the systems and methods of the invention.
Figure 9:
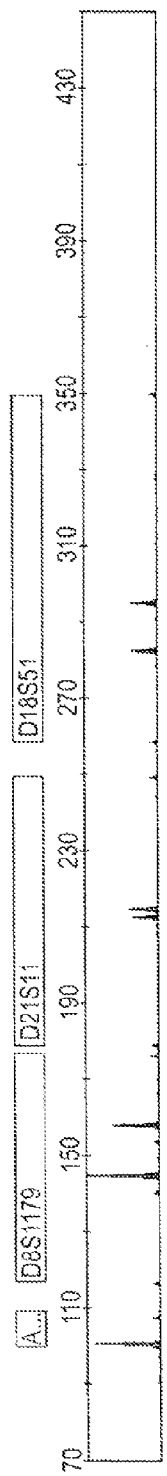
Figure 9:
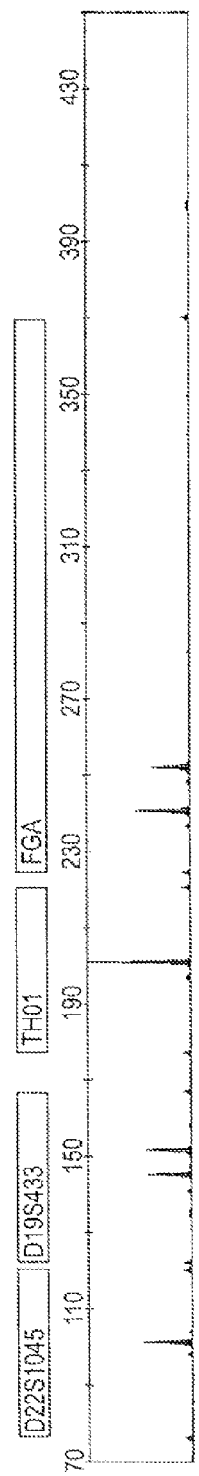
Figure 9:
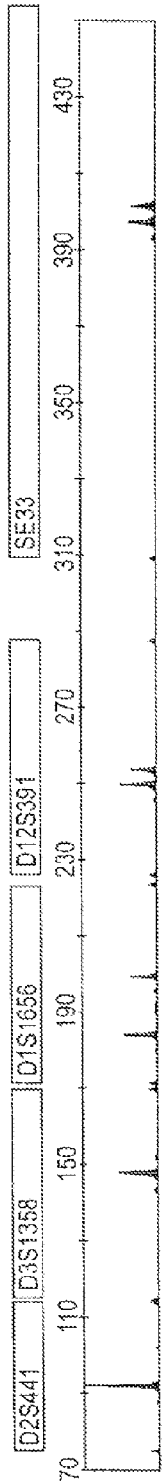

Example 1 illustrates the feasibility of capturing DNA from a fingertip on a transparency film (3M, PP2200) at the same time that a fingerprint image is obtained. An individual is instructed to touch a portion of his face one or several times with the finger to be imaged prior to firmly pressing that finger on a piece of transparency film placed over the scanning portion of a Lumidign optical fingerprint imager. The image of the fingerprint is captured electronically. The unprocessed image is shown in FIG. 6. The quality score assigned by the imaging component is NIST quality score 1, thus providing a fingerprint image of high quality for further electronic processing in any suitable fashion, assignment of minutiae electronic transmittal to another agency, and/or digital storage. The DNA deposited within the fingerprint is subsequently transferred from the transparency film using an "edge swab" to a PCR wellplate for direct STR analysis. To initiate STR analysis, the fingerprint DNA on the transparency film is first transferred onto an edge swab by swabbing the fingerprint three times (swab, FIG. 2A; fingerprint obtained on a substrate as in FIG. 1B). The edge swab is made by wrapping a 20 mm by 100 mm filter paper strip (Whatman, cat #: 3030-6189) over a plastic holder having a narrow edge. The active swabbing area has a dimension of about 1 mm by about 15 mm. After swabbing the fingerprint, the flier paper strip is detached from the swab holder and eight 2 mm diameter punches are generated from the active swabbing area using a Harris Uni-Core punch. Alternatively punches can be generated automatically, for example, by using a BSD punching instrument. Punches are then placed directly into a well of a 96-well PCR plate. 25 ul NGM ®Select Express PCR reaction mix is added to the well containing paper punches. The thermo cycling conditions are 95° C./1 m, 29 cycles of (94° C./3 s, 59° C./16 sec, 65° C./29 sec), 60° C./5 min and 4° C.—hold. After thermal cycling 1 ul PCR amplification product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer; POP4™ polymer and Dye set: G5. The resulting STR electropherogram is analyzed using GeneMapper® ID-X software (Applied Biosystems). Full STR profiles for all 16 STR markers and the sex determination marker Amelogenin is obtained as shown in FIG. 7. From left to right in the uppermost lane, the alleles for D10S1248, vWA, D16S539, and S2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, DS1656, D12S391, and SE33.

Example 2

Example 2 illustrates the feasibility of capturing DNA from a fingertip on a transparency film (3M, PP2200) and the subsequent transfer of fingerprint DNA from transparency film using a paper disc swab to PCR plate for direct STR analysis. To initiate STR analysis, the fingerprint DNA on the tranparency film is first transferred onto a disc swab by swabbing the fingerprint (swab, FIG. 4; fingerprint is obtained on a substrate FIG. 1B, employing the method of depositing a fingerprint described in Example 1). The paper disc swab is made by attaching a 3 mm diameter filter paper disc to the end of 2 mm diameter Harris Uni-Core punch. 3 mm diameter filter paper discs are generated from a sheet of filter paper (Whatman, cat #: 3030-8189). After swabbing of the fingerprint, the paper disc is ejected into a 96-well PCR plate. The fingerprint is swabbed two more times with two additional paper disc swabs and both paper discs are added to the same PCR well containing the first paper disc. 25 ul NGM Select Express PCR reaction mix was added to the well containing paper punches. The thermo cycling conditions are 95 C/1 m, 29 cycles of (94° C./3 s, 59° C./16 sec, 65° C./29 sec), 60° C./5 min and 4° C.—hold. After thermal cycling 1 ul PCR amplification product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherogram is analyzed using GeneMapper® ID-X software (Applied Biosystems). Full STR profiles for all 16 STR markers and the sex determination marker Amelogenin are obtained (FIG. 8) From left to right in the uppermost lane, the alleles for D10S1248, vWA, D16S539, and S2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, DS1656, D12S391, and SE33.

Example 3

Example 3 illustrates the feasibility of capturing DNA from a fingertip on a plain microscope glass slide and the subsequent transfer of fingerprint DNA from a glass slide using an "edge swab" to PCR plate for direct STR analysis. To initiate STR analysis, the fingerprint DNA on the glass slide is first transferred onto a edge swab by swabbing the fingerprint three times (swab, FIG. 2A; the fingerprint is obtained on a glass substrate as in FIG. 1B. The method of obtaining the fingerprint is as described in Example 1.). The edge swab is made by wrapping a 15 mm by 100 mm filter paper strip (Whatman, cat #: 3030-6189) over a plastic holder. The active swabbing area has the dimensions of about 1 mm by about 15 mm. After swabbing the fingerprint, the filer paper strip is detached from the swab holder and eight 2 mm diameter punches are generated from the active swabbing area using a Harris Uni-Core punch. Alternatively punches can be generated automatically using a BSD punching machine. Punches are then placed directly into a well of a 96-well PCR plate. 25 ul NGM® Select Express PCR reaction mix is added to the wells containing the paper punches. The thermo cycling conditions are 95° C./1 m, 29 cycles of (94° C./3 s, 59° C./18 sec, 65° C./29 sec), 60° C./5 min and 4° C.—hold. After thermal cycling 1 ul PCR product from each sample is mixed with GeneScan®500 size standard and deionized formamide and analyzed using a ABI 3130xl capillary electrophoresis instrument using the following conditions; Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherogram is analyzed using GeneMapper® ID-X software (Applied Biosystems). Full STR profiles for all 16 STR markers and the sex determination marker Amelogenin are obtained (FIG. 9) From left to right in the uppermost lane, the alleles for D10S1248, vWA, D16S539, and S2S1138 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, DS1656, D12S391, and SE33.

Example 4

Figure 10:
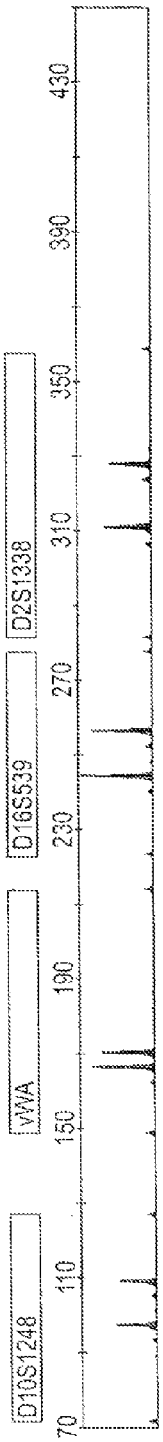
FIG. 10 is a graphical representation of a STR analysis obtained from an individual according to the systems and methods of the invention.
Figure 10:
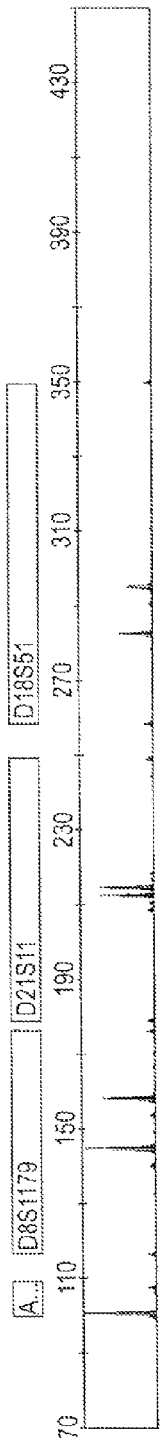
Figure 10:
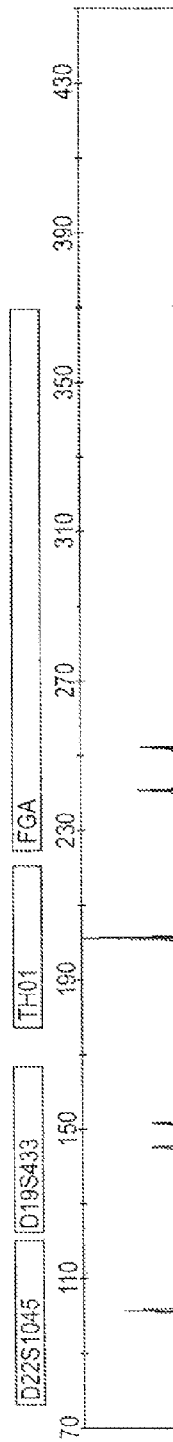
Figure 10:
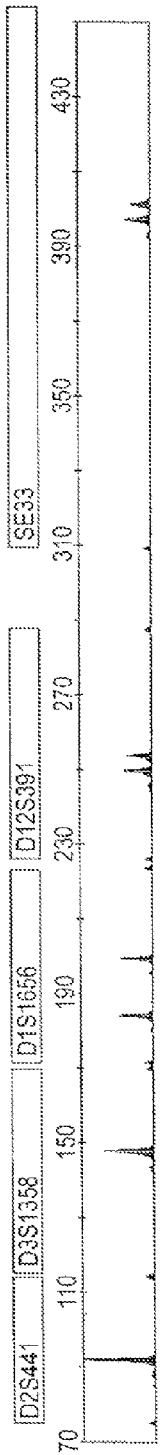

Example 4 illustrates the feasibility of capturing DNA from a fingertip on a plain glass microscope slide with subsequent rinsing of fingerprint DNA on slide using STR PCR reaction mix for direct STR analysis. A fingerprint is obtained on an untreated glass microscope slide, using the method described in Example 1. To obtain nucleic acids from the fingerprint and perform STR analysis, 40 ul of NGM® Select Express PCR reaction mix is pipetted on to the fingerprint DNA on the glass slide and is spread out to cover the entire fingerprint. Using a pipette tip, the PCR reaction mix is agitated. About 25 ul of the PCR reaction mix, including nucleic acids from the fingerprint, is recovered and transferred into a well of a 96-well PCR plate. The thermo cycling conditions are 95° c./1 m, 29 cycles of (94° C./3 s, 59° C./16 sec, 85° C./29 sec), 60° C./5 min and 4° C.—hold. After thermal cycling 1 ul PCR product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherogram is analyzed using GeneMapper® ID-X software (Applied Biosystems). Full STR profiles for all 16 STR markers and the sex determination marker Amelogenin was obtained, as shown in FIG. 10. From left to right in the uppermost lane, the alleles for D10S1248, vWA, D16S539, and S2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, DS1656, D12S391, and SE33.

Example 5

Figure 11:
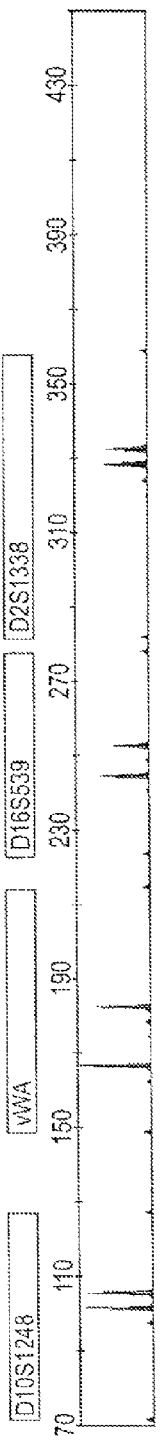
FIG. 11 is a graphical representation of a STR analysis obtained from an individual according to the systems and methods of the invention.
Figure 11:
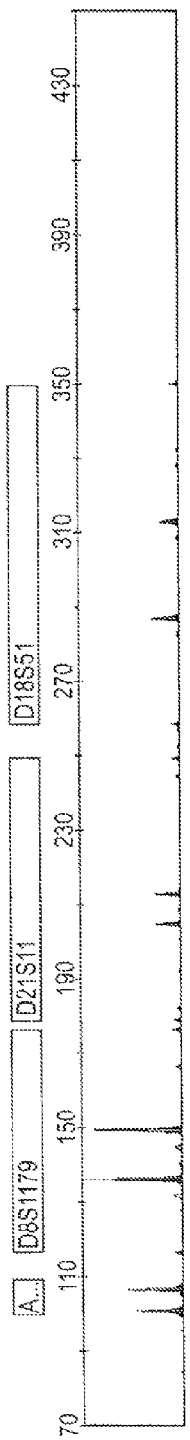
Figure 11:
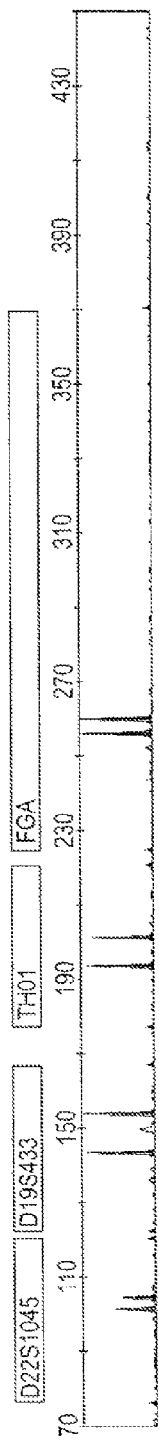
Figure 11:
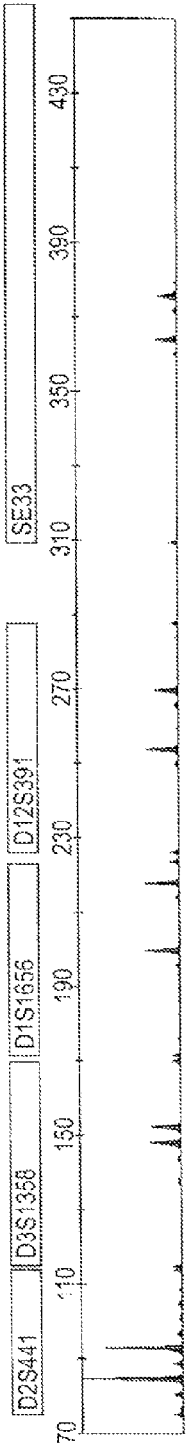

Example 5 illustrates the feasibility of capturing DNA from a fingertip on a transparency film (3M, PP2200) with subsequent rinsing of the fingerprint DNA on the transparency film using STR PCR reaction mix for direct STR analysis. A fingerprint is obtained on the transparency film, using the method described in Example 1. To obtain nucleic acids from the fingerprint and perform a STR analysis, 40 ul of NGM ®Select Express PCR reaction mix is pipetted on to the fingerprint DNA on the tranparency film and is spread out to cover the entire fingerprint. Using a pipette tip, the PCR reaction mix is agitated. About 25 ul of PCR reaction mix is recovered and transferred into a well of a 96-well PCR plate. The thermo cycling conditions are 95° C./1 m, 29 cycles of (94° C./3 s, 59° C./16 sec, 85° C./29 sec), 60° C./5 min and 4° C.—hold. After thermal cycling 1 ul PCR product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, and Run: 15 kV, 1500 s, Capillary length: 36 cm, Separation polymer: POP4™ polymer and Dye set: G5. The resulting STR electropherogram is analyzed using GeneMapper® ID-X software (Applied Biosystems). Full STR profiles for all 16 STR markers and the sex determination marker Amelogenin are obtained as shown in FIG. 11. From left to right in the uppermost lane, the alleles for D10S1248, vWA, D15S539, and S2S1338 are shown; the second lane from the top of the page shows the alleles for Amelogenin, D8S1179, D21S11, and D18S51; the third lane from the top shows the alleles for D22S1045, D19S433, TH01, and FGA; and the bottom panel shows the alleles for D2S441, D3S1358, DS1656, D12S391, and SE33.

Example 6

Figure 12:
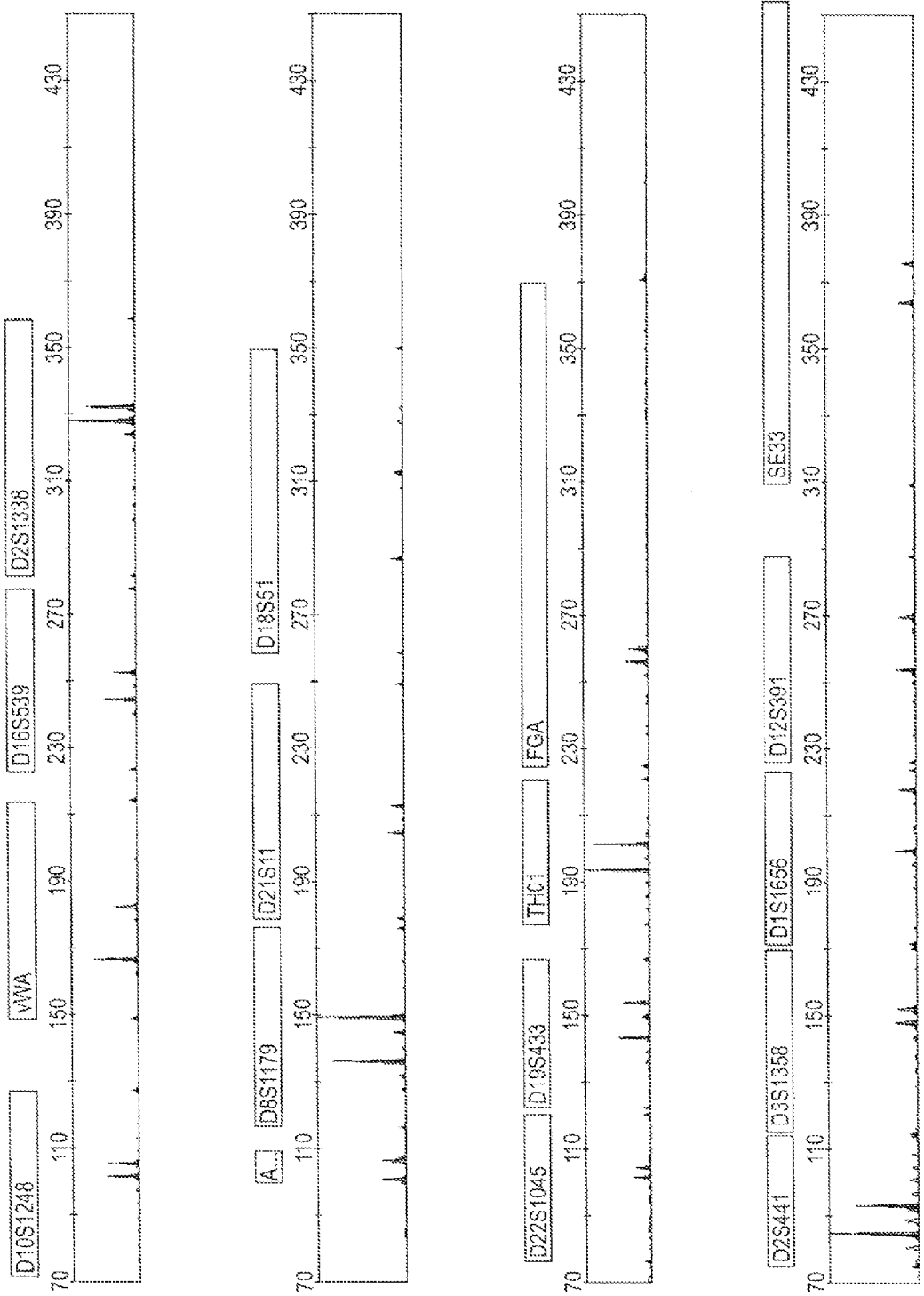
FIG. 12 is a graphical representation of a STR analysis obtained from an individual according to the systems and methods of the invention.

Example 6 illustrates the feasibility of capturing DNA from a fingertip on a MicroAmp®Clear Adhesive Film (Life Tech, 4306311) with subsequent rinsing of fingerprint DNA on the adhesive film using STR PCR reaction mix for direct STR analysis. A fingerprint is obtained on the adhesive film, using the method described in Example 1 to obtain nucleic acids from the fingerprint and perform a STR analysis, 50 ul of NGM Select Express PCR reaction mix is pipetted on to the fingerprint DNA on the adhesive film and is spread out to cover the entire fingerprint. Using a pipette tip, the PCR reaction mix is agitated. About 25 ul of PCR reaction mix is recovered and transferred into a well of a 96-well PCR plate. The thermo cycling conditions are 95° C./1 m, 29 cycles of (94° C./3 s, 59° C/16 sec, 65° C./29 sec), 60° C./5 min and 4° C.—hold. After thermal cycling 1 ul PCR product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherogram is analyzed using GeneMapper® ID-X software (Applied Biosystems). Full STR profiles for all 16 STR markers and the sex determination marker Amelogenin are obtained as shown in FIG. 12.

Example 7

Example 7 illustrates the ability to obtain DNA from a fingerprint on a transparency film (3M, PP2200), with subsequent transfer for direct PCR amplification, using an edge swab (FIG. 17-1) assisted with ethanol. The edge swab is made by wrapping a 5 mm by 80 mm filter paper strip (Whatman, cat #: 3030-6189) over a plastic handling component having a narrow active collection surface area supported by a protruding portion of the support portion of the handling component of the swab. The active swabbing area (active collection surface area) has a dimension of about 1 mm by about 5 mm width.

A fingerprint is obtained on the transparency film, using the method described in Example 1. The fingerprint is swabbed using the edge swab, with the addition of about 20 ul ethanol to assist in collection of nucleic acids from the fingerprint. After swabbing, the swab is allowed to air dry for about four minutes.

Figure 13:
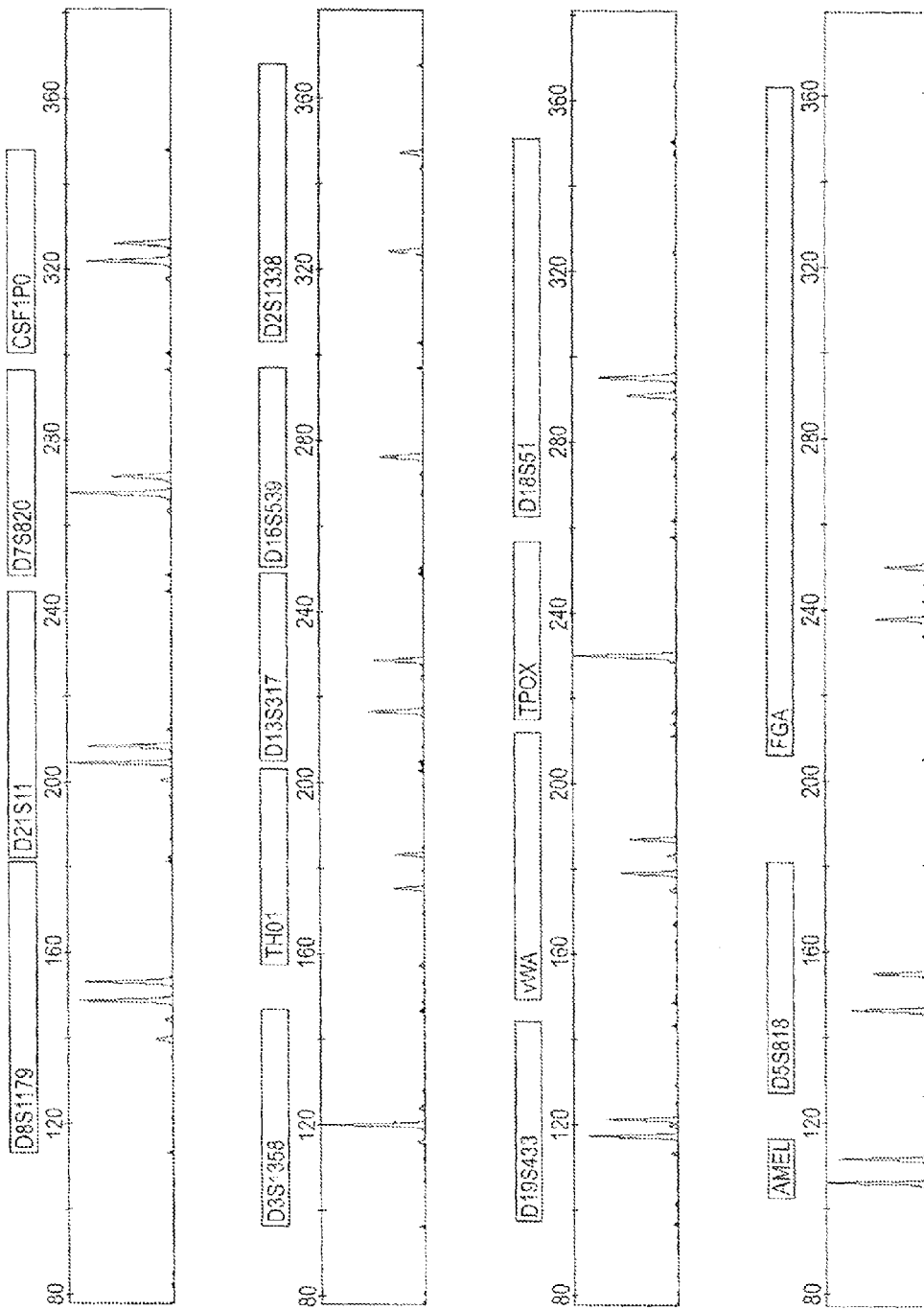
FIG. 13 is a graphical representation of a STR analysis obtained from an individual according to the systems and methods of the invention.

After air drying, the active collection component strip is detached from the handling component and two 2 mm diameter punches are generated from the active collection surface area using a Harris Uni-Core punch. Alternatively punches can be generated automatically, for example, by using a BSD punching instrument. Punches are then placed directly into a well of a 96-well PCR plate. 7 ul PCR reaction mix, which includes GlobalFiler® Master Mix and Identifiler® Direct primer mix, is added to the well containing the paper punches. The thermo cycling conditions are 95° C./1 m, 29 cycles of (94° C./10 s, 59° C./90 sec), 60° C./10 min and 4° C.—hold. After thermal cycling 1 ul PCR product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherograms are analyzed using GeneMapper® ID-X software (Applied Biosystems). A full STR profile is obtained as shown in FIG. 13.

The alleles for each electropherogram using primers provided by the Identifiler Direct® PCT reaction mix are as follows:

First panel, from left to right: D8S1179; D21S11; D7S820; and CSF1PO. Second panel, from left to right: D3S1358; THO1; D13S317; D16S539; and D2S1338. Third panel: D19S433; vWA; TPOS; and D18S51. Fourth panel, from left to right: Amelogenin, D5S818, and FGA.

Example 8

Example 8 illustrates the ability to obtain DNA from a fingerprint on a transparency film (3M, PP2200), with subsequent transfer for direct PCR amplification, using an edge swab (FIG. 17A) assisted with water. The edge swab is made by wrapping a 5 mm by 80 mm filter paper strip (Whatman, cat #: 3030-8189) over a plastic handling component having a narrow active collection surface area supported by a protruding portion of the support portion of the handling component of the swab. The active swabbing area (active collection surface area) has a dimension of about 1 mm by about 5 mm width.

A fingerprint is obtained on the transparency film, using the method described in Example 1. The fingerprint is swabbed using the edge swab, with the addition of about 20 ul water to assist in collection of nucleic acids from the fingerprint. After swabbing, the swab is allowed to air dry for a few minutes.

Figure 14:
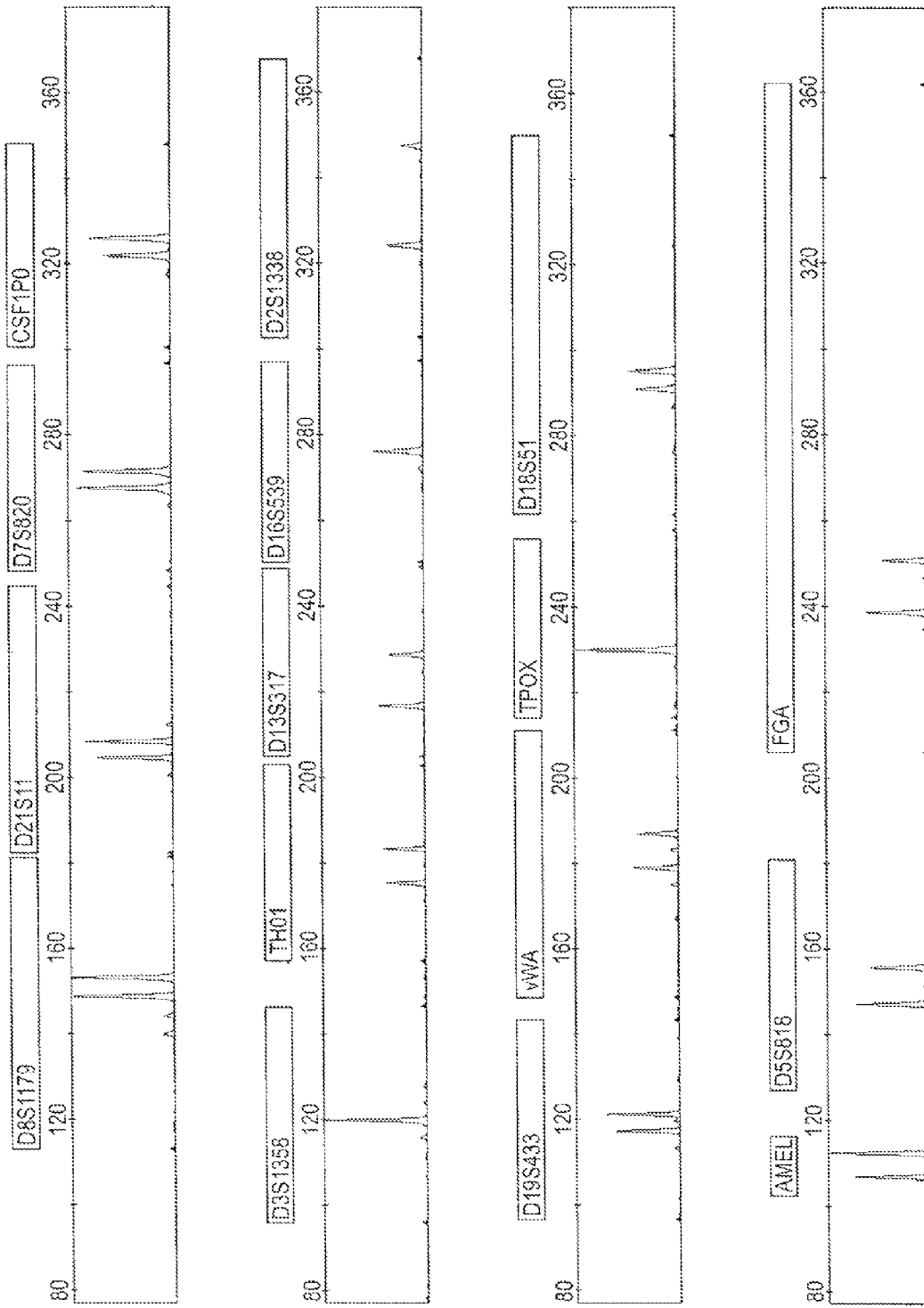
FIG. 14 is a graphical representation of a STR analysis obtained from an individual according to the systems and methods of the invention.

After air drying, the active collection component strip is detached from the handling component and two 2 mm diameter punches are generated from the active collection surface area using a Harris Uni-Core punch. Alternatively punches can be generated automatically, for example, by using a BSD punching instrument. Punches are then placed directly into a well of a 96-well PCR plate. 7 ul PCR reaction mix, which includes GlobalFiler® Master Mix and Identifiler® Direct primer mix, is added to the well containing the paper punches. The thermo cycling conditions are 95° C./1 min, 29 cycles of (94° C./10 s, 59° C./90 sec), 60° C./10 min and 4° C.—hold. After thermal cycling 1 ul PCR product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherograms are analyzed using GeneMapper® ID-X software (Applied Biosystems). A full STR profile is obtained as shown in FIG. 14.

The alleles for each electropherogram using primers provided by the Identifiler Direct® PCR reaction mix are as follows:

First panel, from left to right: D8S1173; D21S11; D7S820; and CSF1PO. Second panel, from left to right: D3S1358; TH01; D13S317; D16S539; and D2S1338. Third panel: D19S433; vWA; TPOS; and D18S51. Fourth panel, from left to right: Amelogenin, D5S818, and FGA.

Example 9

Example 9 illustrates the ability to obtain DNA from a fingerprint on a transparency film (3M, PP2200), with subsequent transfer for direct PCR amplification, using an edge swab (FIG. 17A) assisted with acetonitrile. The edge swab is made by wrapping a 5 mm by 80 mm filter paper strip (Whatman, cat #: 3030-8189) over a plastic handling component having a narrow active collection surface area supported by a protruding portion of the support portion of the handling component of the swab. The active swabbing area (active collection surface area) has a dimension of about 1 mm by about 5 mm width.

A fingerprint is obtained on the transparency film, using the method described in Example 1. The fingerprint is swabbed using the edge swab, with the addition of about 15 ul acetonitrile to assist in collection of nucleic acids from the fingerprint. After swabbing, the swab is allowed to air dry for a few minutes.

Figure 15:
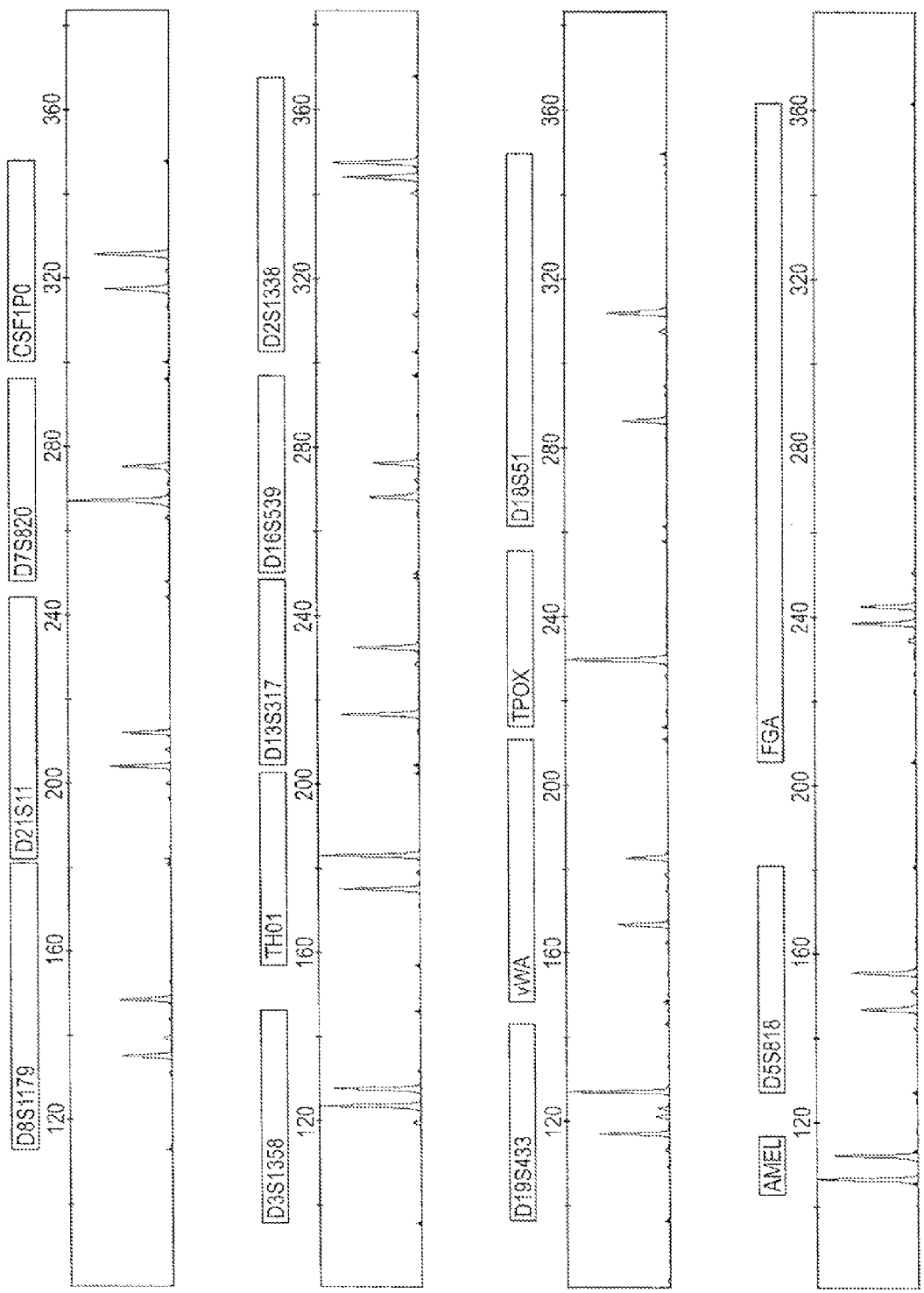
FIG. 15 is a graphical representation of a STR analysis obtained from an individual according to the systems and methods of the invention.

After air drying, the active collection component strip is detached from the handling component and two 2 mm diameter punches are generated from the active collection surface area using a Harris Uni-Core punch. Alternatively punches can be generated automatically, for example, by using a BSD punching instrument. Punches are then placed directly into a well of a 96-well PCR plate. 7 ul PCR reaction mix, which includes GlobalFiler® Master Mix and Identifiler® Direct primer mix, is added to the well containing the paper punches. The thermo cycling conditions are 95° C./1 m, 29 cycles of (94° C./10 s, 59° C./90 sec), 60° C./10 min and 4° C.—hold. After thermal cycling 1 ul PCR product from each sample is mixed with GeneScan®500 size standard and deionized formamide and analyzed using a ABI 3130xl capillary electrophoresis instrument using the following conditions: Oven: 60° C., Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherograms are analyzed using GeneMapper® ID-X software (Applied Biosystems). A full STR profile is obtained as shown in FIG 15.

The alleles for each electropherogram using primers provided by the Identifiler Direct® PCR reaction mix are as follows:

First panel, from left to right: D8S1179; D21S11; D7S820; and CSF1PO. Second panel, from left to right: D3S1358; TH01; D13S317; D16S539; and D2S1338. Third panel; D19S433; vWA; TPOS; and D18S51. Fourth panel, from left to right: Amelogenin, D5S818, and FGA.

While the foregoing specification teaches the principles of the present invention, with examples provided for the purpose of illustration, it will be appreciated by one skilled in the art from reading this disclosure that various changes in form and detail can be made without departing from the spirit and scope of the invention.

What is claimed:

1. A device comprising:
   a collection component; and
   a handling component;
   wherein the collection component is detachably connected to the handling component; and
   wherein the collection component comprises an active collection surface area encompassing an exterior edge of an angled fold of the collection component, the angled fold formed over a first portion of the handling component
   and wherein the active collection surface area:
   a) can collect a biological sample from an appendage placed on at least a first surface area of a substrate made of a polymeric film or a glass, wherein the active collection surface area is at least 50% smaller than the first surface area of the substrate; and
   b) allows direct nucleic acid amplification reaction of the biological sample collected in the active collection surface area or a portion thereof.

2. The device of claim 1, wherein a portion of the active collection surface area can be punched out and used for archiving.

3. The device of claim 1, wherein the collection component comprises fibrous material and wherein the fibrous material comprises natural fibers, synthetic polymeric fibers or a combination thereof.

4. The device of claim 3, wherein the fibrous material is cotton, paper, nitrocellulose paper, nylon paper, cellulose paper, cotton paper, polyester papers, and combinations thereof and optionally, wherein the fibrous material is chemically treated.

5. The device of claim 1, wherein the first portion of the handling component further comprises a layer of absorbent material underlying the collection component.

6. The device of claim 1, wherein the first portion of the handling component comprises a stiffening support for the collection component.

7. The device of claim 1, wherein a length of the collection component along the angled fold is about 20 mm or less.

8. The device of claim 1, wherein the exterior edge of the angled fold forms an acute angle.

9. The device of claim 1, wherein the active collection surface area or a punched out portion thereof can fit within an amplification reaction volume of about 2 ul to about 100 ul.

10. A kit comprising the device of claim 1, and optionally, instructions for its use.

11. The kit of claim 10, further comprising reagents for stabilizing the biological sample for archiving or shipping.

12. The kit of claim 10, further comprising reagents for amplification of the at least one nucleic acid of the biological sample.

13. The kit of claim 10, further comprising at least one enclosure to protect the collection component from contamination while archiving or shipping.

14. The kit of claim 10, wherein the collection component, the handling component, or both comprise an identifier to associate the sample with the substrate from which the sample was collected, wherein the identifier is alphanumeric, graphical, magnetic, or electromagnetic.

15. A system comprising:
   a. at least a first imaging component comprising a scanning surface configured to permit an energy wave to penetrate the scanning surface, wherein the energy wave is configured to image the at least one ridge and valley signature of an appendage of the individual; and
   b. a substrate having at least a first surface area, wherein the substrate is configured to: a) permit the energy wave to penetrate the substrate to image the appendage in contact with the substrate; and b) collect the biological sample from the appendage; wherein the system is configured to collect at least one ridge and valley signature by imaging the appendage through the scanning surface and the substrate while the appendage is positioned upon the substrate; and
   c. the device of claim 1.

16. The system of claim 15, further comprising a processor configured to transmit the ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control and any combination thereof.

17. A method comprising:
   d. providing at least a first imaging component configured to provide an energy wave and comprising a scanning surface configured to permit the energy wave to penetrate the scanning surface;
   e. providing a substrate configured to collect a biological sample from an appendage of the individual and configured to permit the energy wave to penetrate the scanning surface, wherein the substrate is positioned over the scanning surface;
   f. positioning the appendage of the individual upon the substrate, thereby depositing the biological sample upon the substrate;
   g. collecting the at least one ridge and valley signature from the appendage imaged by the energy wave; and
   h. collecting the biological sample from the substrate using the device of claim 1.

18. The method of claim 17, wherein the substrate or the sample concentration device is prewetted with ethanol, water, or acetonitrile when concentrating the biological sample from the substrate to the sample concentration device.

19. The method of claim 17, further comprising the step of providing an identifier to associate the biological sample of the individual with the at least one ridge and valley signature of the individual, wherein the identifier is alphanumeric, graphical, magnetic, or electromagnetic.

20. The method of claim 17, further comprising the step of shipping the substrate containing the biological sample to another location for archiving or testing.

21. The method of claim 17, further comprising the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

22. The method of comprising subjecting the biological sample to an analysis, wherein the analysis is at least one of a polymerase chain reaction, a DNA sequencing reaction, STR analysis, SNP analysis, or Indel analysis.

23. The method of claim 22, further comprising the step of transmitting the identification of the individual provided by the analysis to at least one of a law enforcement agency, immigration control agency, forensics investigative agency, access control agency, licensing agency, or financial services agency.

* * * * *